(12) United States Patent
Ichikawa et al.

(10) Patent No.: US 7,883,477 B2
(45) Date of Patent: Feb. 8, 2011

(54) HUMAN BODY BACKBONE MEASURING/DISPLAYING SYSTEM

(75) Inventors: Eiichi Ichikawa, Fukushima (JP);
Morio Ichikawa, Fukushima (JP)

(73) Assignees: Nihon University, Tokyo (JP);
MASARU SEIKI Corporation, Tamura-gun (JP)

( * ) Notice: Subject to any disclaimer, the term of this patent is extended or adjusted under 35 U.S.C. 154(b) by 656 days.

(21) Appl. No.: 11/718,368

(22) PCT Filed: Oct. 26, 2005

(86) PCT No.: PCT/JP2005/019683

§ 371 (c)(1),
(2), (4) Date: Feb. 1, 2008

(87) PCT Pub. No.: WO2006/049057

PCT Pub. Date: May 11, 2006

(65) Prior Publication Data

US 2008/0208080 A1    Aug. 28, 2008

(30) Foreign Application Priority Data

Nov. 1, 2004    (JP) .......................... 2004-317640

(51) Int. Cl.
*A61B 5/103* (2006.01)
*A61B 5/117* (2006.01)
*G01C 9/00* (2006.01)
*G01C 17/00* (2006.01)
*G01C 19/00* (2006.01)

(52) U.S. Cl. ................... 600/594; 600/587; 702/151

(58) Field of Classification Search ................ 600/594, 600/587; 702/151
See application file for complete search history.

(56) References Cited

U.S. PATENT DOCUMENTS

| 889,224 | A | * | 6/1908 | Haas | ............................ 600/594 |
| 1,234,527 | A | * | 7/1917 | Berriman | .................... 33/514.2 |
| 1,271,461 | A | * | 7/1918 | Hanna | ........................ 33/23.09 |

(Continued)

FOREIGN PATENT DOCUMENTS

JP    6 7325    1/1994

(Continued)

*Primary Examiner*—Max Hindenburg
*Assistant Examiner*—Sean P Dougherty
(74) *Attorney, Agent, or Firm*—Oblon, Spivak, McClelland, Maier & Neustadt, L.L.P.

(57) ABSTRACT

A human spinal column measuring and displaying system includes a spinal column measuring apparatus capable of measuring bending or a circumflex (twist) angle of the spinal column of the human body as a detaching amount measuring data from a reference value, an input apparatus for inputting gender, height data of the measurement subject, an image processing apparatus for inputting the detaching amount measuring data from the spinal column measuring apparatus and data from the input apparatus and generating a three-dimensional spinal column image of the measurement subject based on the detaching amount measuring data and the gender, height data of the measurement subject, and a display apparatus for displaying an image data from the image processing apparatus. The system can calculate a measured data of three-dimensional coordinates and a circumflex angle of the spinal column by scanning a predetermined probe along the spinal column, and simulate a shape of the spinal column from the measured data to be able to display a three-dimensional pseudonymous spinal column image by utilizing computer graphics.

16 Claims, 33 Drawing Sheets

U.S. PATENT DOCUMENTS

| | | | |
|---|---|---|---|
| 1,571,140 A * | 1/1926 | O'Connor | 33/515 |
| 2,111,648 A * | 3/1938 | Stone | 33/512 |
| 2,162,916 A * | 6/1939 | Hyland | 33/3 C |
| 4,425,713 A * | 1/1984 | Rotella | 33/515 |
| 4,444,204 A * | 4/1984 | Bryant et al. | 600/594 |
| 5,101,835 A * | 4/1992 | DelRe | 600/594 |
| 5,156,162 A * | 10/1992 | Gerhardt | 600/594 |
| 5,533,084 A * | 7/1996 | Mazess | 378/54 |
| 6,038,281 A * | 3/2000 | Mazess | 378/54 |
| 6,468,233 B2 * | 10/2002 | Cook | 600/594 |
| 6,539,328 B1 | 3/2003 | Gremonese et al. | |
| 7,131,952 B1 * | 11/2006 | Dickholtz et al. | 600/594 |
| 7,439,978 B2 * | 10/2008 | Oumi | 345/443 |
| 2002/0049393 A1 * | 4/2002 | Cook | 600/594 |
| 2002/0133097 A1 * | 9/2002 | Leitner et al. | 600/594 |
| 2002/0133098 A1 * | 9/2002 | Shechtman et al. | 600/594 |
| 2003/0220590 A1 * | 11/2003 | Csonka | 600/594 |
| 2005/0148839 A1 * | 7/2005 | Shechtman et al. | 600/407 |
| 2007/0242869 A1 * | 10/2007 | Luo et al. | 382/132 |

FOREIGN PATENT DOCUMENTS

| | | |
|---|---|---|
| JP | 3037703 | 3/1997 |
| WO | 03 017839 | 3/2003 |

* cited by examiner

Fig. 7a

MEASURE VALUE OF MALE VERTEBRAE

| | BELLY SIDE HEIGHT AVERAGE VALUE ± STANDARD DEVIATION | BACK SIDE HEIGHT AVERAGE VALUE ± STANDARD DEVIATION | UPPER FACE ARROW SHAPE DIAMETER AVERAGE VALUE ± STANDARD DEVIATION | LOWER FACE ARROW SHAPE DIAMETER AVERAGE VALUE ± STANDARD DEVIATION | UPPER FACE LATERAL DIAMETER AVERAGE VALUE ± STANDARD DEVIATION | LOWER FACE LATERAL DIAMETER AVERAGE VALUE ± STANDARD DEVIATION |
|---|---|---|---|---|---|---|
| THIRD CERVICAL VERTEBRA (C3) | 12.39 ± 1.45 | 12.39 ± 1.41 | 15.23 ± 0.93 | 16.41 ± 1.41 | 20.44 ± 1.38 | 20.60 ± 2.47 |
| FOURTH CERVICAL VERTEBRA (C4) | 12.24 ± 1.21 | 12.15 ± 1.24 | 15.63 ± 1.47 | 18.59 ± 1.40 | 21.95 ± 1.84 | 21.91 ± 2.25 |
| FIFTH CERVICAL VERTEBRA (C5) | 11.42 ± 1.19 | 11.76 ± 1.18 | ...... | ...... | ...... | ...... |
| SIXTH CERVICAL VERTEBRA (C6) | 11.69 ± 1.37 | 12.05 ± 1.27 | | | | |
| SEVENTH CERVICAL VERTEBRA (C7) | 13.79 ± 1.16 | 13.38 ± 1.21 | | | | |
| ... | ... | ... | | | | |
| FIRST LUMBAR VERTEBRA (L1) | 23.39 ± 1.80 | | | | | |
| SECOND LUMBAR VERTEBRA (L2) | 24.38 ± 2.09 | | | | | |
| THIRD LUMBAR VERTEBRA (L3) | 24.81 ± 1.82 | | | | | |
| FOURTH LUMBAR VERTEBRA (L4) | 24.89 ± 2.02 | | | | | |
| FIFTH LUMBAR VERTEBRA (L5) | 25.15 ± 2.29 | | | | | |

*Fig. 7b*

MEASURE VALUE OF FEMALE VERTEBRAE

| | BELLY SIDE HEIGHT AVERAGE VALUE ± STANDARD DEVIATION | BACK SIDE HEIGHT AVERAGE VALUE ± STANDARD DEVIATION | UPPER FACE ARROW SHAPE DIAMETER AVERAGE VALUE ± STANDARD DEVIATION | LOWER FACE ARROW SHAPE DIAMETER AVERAGE VALUE ± STANDARD DEVIATION | UPPER FACE LATERAL DIAMETER AVERAGE VALUE ± STANDARD DEVIATION | LOWER FACE LATERAL DIAMETER AVERAGE VALUE ± STANDARD DEVIATION |
|---|---|---|---|---|---|---|
| THIRD CERVICAL VERTEBRA (C3) | 12.28 ± 1.23 | 11.71 ± 1.46 | 14.55 ± 1.46 | 15.53 ± 1.77 | 19.24 ± 1.43 | 19.80 ± 1.80 |
| FOURTH CERVICAL VERTEBRA (C4) | 11.61 ± 1.17 | 11.30 ± 1.42 | 14.98 ± 1.59 | 15.46 ± 1.59 | 20.81 ± 1.76 | 20.66 ± 2.11 |
| FIFTH CERVICAL VERTEBRA (C5) | 11.36 ± 1.53 | 11.51 ± 1.57 | ......... | ......... | ......... | ......... |
| SIXTH CERVICAL VERTEBRA (C6) | 11.43 ± 1.33 | 11.59 ± 1.50 | | | | |
| SEVENTH CERVICAL VERTEBRA (C7) | 13.22 ± 1.19 | 12.83 ± 1.23 | | | | |
| ... | ... | ... | | | | |
| FIRST LUMBAR VERTEBRA (L1) | 23.76 ± 1.94 | | | | | |
| SECOND LUMBAR VERTEBRA (L2) | 24.66 ± 2.00 | | | | | |
| THIRD LUMBAR VERTEBRA (L3) | 24.69 ± 2.22 | | | | | |
| FOURTH LUMBAR VERTEBRA (L4) | 24.59 ± 2.09 | | | | | |
| FIFTH LUMBAR VERTEBRA (L5) | 25.85 ± 2.11 | | | | | |

Fig. 11
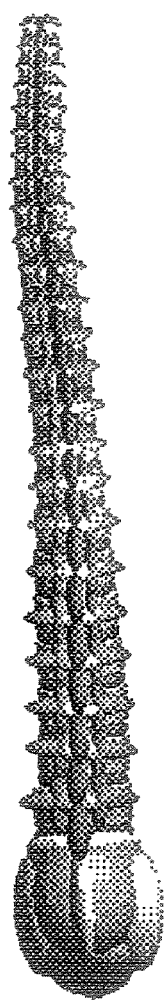 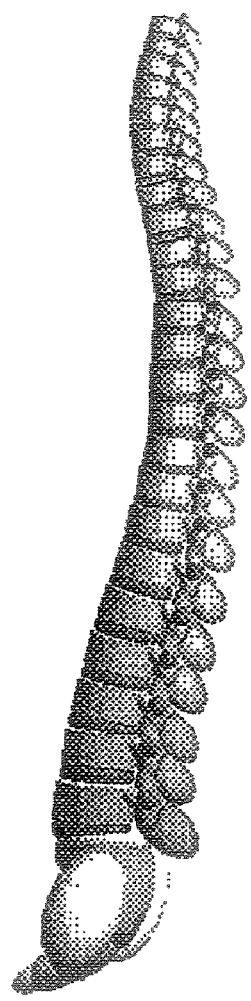
(a)  (b)

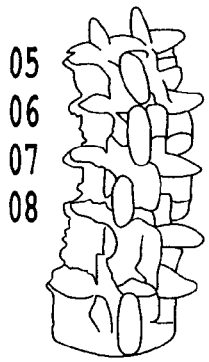

I : angle information at respective intervertebral disks
II : upper thoracic vertebrae (four bodies)
   [001] front/rear bent   [002]: left/right inclination
   [003]: circumflex
III : first thoracic vertebra → second thoracic vertebra
   [004]: front bent 0.4 degrees   [005]: right lower 11.1 degrees
   [006]: right rear 2.8 degrees
IV : second thoracic vertebra → third thoracic vertebra
   [007]: rear bent 0.1 degrees   [008]: right lower 9.6 degrees
   [009]: right rear 6.7 degrees
V : third thoracic vertebra → fourth thoracic vertebra
   [010]: rear bent 0.1 degrees   [011]: right lower 9.4 degrees
   [012]: right front 8.6 degrees
VI : fourth thoracic vertebra → fifth thoracic vertebra
   [013]: rear bent 0.1 degrees   [014]: right upper 14.5 degrees
   [015]: right front 3.7 degrees

*Fig. 12a*

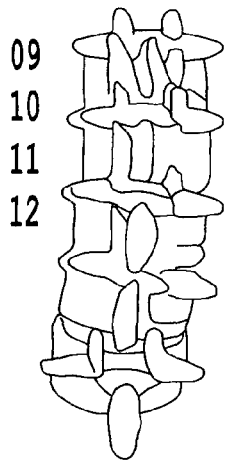

I : angle information at respective intervertebral disks
II : middle thoracic vertebrae (four bodies)
   [001] front/rear bent   [002]: left/right inclination
   [003]: circumflex
III : fifth thoracic vertebra → sixth thoracic vertebra
   [004]: front bent 11.7 degrees   [005]: right lower 0.1 degrees
   [006]: right rear 2.1 degrees
IV : sixth thoracic vertebra → seventh thoracic vertebra
   [007]: front bent 10.1 degrees   [008]: right lower 5.9 degrees
   [009]: right rear 0.3 degrees
V : seventh thoracic vertebra → eighth thoracic vertebra
   [010]: front bent 5.4 degrees [011]: right lower 5.6 degrees
   [012]: right front 2.4 degrees
VI : eighth thoracic vertebra → ninth thoracic vertebra
   [013]: front bent 22.8 degrees   [014]: right upper 10.4 degrees
   [015]: right front 1.8 degrees

*Fig.12b*

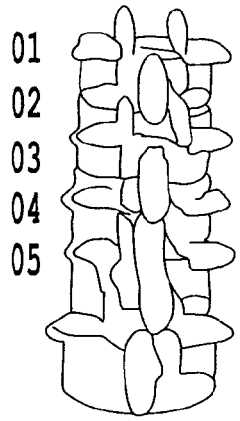

I : angle information at respective intervertebral disks
II : lumber vertebrae (five bodies)
   [001] front/rear bent   [002]: left/right inclination
   [003]: circumflex
III : fifth lumber vertebra → second lumber vertebra
   [004]: front bent 15.3 degrees   [005]: right lower 0.0 degrees
   [006]: right rear 1.2 degrees
IV : second lumber vertebra → third lumber vertebra
   [007]: rear bent 5.3 degrees   [008]: right lower 0.0 degrees
   [009]: right rear 1.8 degrees
V : third lumber vertebra → fourth lumber vertebra
   [010]: rear bent 14.2 degrees   [011]: right upper 0.0 degrees
   [012]: right rear 7.0 degrees
VI : fourth lumber vertebra → fifth lumber vertebra
   [013]: front bent 0.0 degrees   [014]: right lower 0.0 degrees
   [015]: right rear 7.0 degrees

*Fig. 12c*

HUMAN BODY BACKBONE MEASURING/DISPLAYING SYSTEM

TECHNICAL FIELD

The present invention relates to a human spinal column measuring and displaying system capable of measuring bending of the spinal column of the human body by a simple and convenient method and capable of displaying the spinal column on a display screen in a real mode based on a measured value thereof.

BACKGROUND ART

It has conventionally been known that when warping or bending is present at the spinal column, it effects various influences such as diseases of the internal organs the stiffness in the shoulder and the headache on the human body. Therefore, in order to confirm whether improper bending is present at the spinal column, there are used (1) a manual method of confirming whether the spinal column is improperly bent by examining the spinal column position of the human body by touching by a physician of the chiropractic, (2) a method of using Moire topography capable of optically recognizing whether a Moire pattern symmetrical in left and right direction is described on the surface of the human body by irradiating the human body with Moire light and (3) a method of using thermography capable of detecting temperature of the surface of the human body caused by a failure in blood flow and optically recognizing warping of the body (bending of the spinal column) by a distribution of the temperature.

Further, when it is found that bending is present at the spinal column, an image of the Moire topography or the thermography is made to be seen by a patient and an explanation stating "the spinal column is bent to the right or to the left" is given from a surface state of the human body. Further, in diagnosis by touching, an explanation is orally given to a patient of a result of the diagnosis by touching.

Further, a predetermined treatment is carried out from the surface of the human body to the bent spinal column by manual therapy by the physician to thereby correct or improve the bending of the spinal column.

Patent Reference 1: JP-A-11-211434

DISCLOSURE OF THE INVENTION

Problems that the Invention is to Solve

However, according to the above-described background art method, in explaining a state of the spinal column liver to the patient (measured subject), only the oral explanation is given to the patient and therefore, a specific bent state of the spinal column cannot be known. Further, in order to know a specific degree of the bending of the spinal column from a display content of the image of the Moire topography or the thermography, skill is required to grasp the display content and it is difficult to know the bent degree of the spinal column simply by a nonprofessional person.

Further, even when the bent spinal column is diagnosed by touching and thereafter a result of carrying out the predetermined treatment is explained, the diagnosis by touching or the treatment per se is much dependent on the technique and the experience of the physician and for the patient (measured subject) even when the degree of correcting the spinal column is explained, it is difficult to understand the specific state of the bending such as how much which portion of the spinal column is bent in which direction, or how much the bending of the spinal column is corrected after the treatment. That is, in explaining orally of the bent state of the spinal column by the physician, a specialized expression is given such that, for example, "number XX of the upper thoracic vertebrae becomes so and so." and there poses a problem that it is difficult to understand how which of the thoracic vertebrae of one's own is bent.

In addition thereto, there poses a problem that it is further difficult to know in details a bent state of each of the spinal column.

The invention has been carried out in view of the above-described situation of the background art and it is an object thereof to provide a human spinal column measuring and displaying system capable of calculating a measured data of three-dimensional coordinates and circumflex values of the spinal column by scanning a predetermined probe along the spinal column and capable of displaying a three-dimensional pseudonymous spinal column by simulating a shape of the spinal column from the measured data and utilizing a compute graphics.

Means for Solving the Problems

In order to achieve the above-described and other objects, a human spinal column measuring and displaying system according to the present invention comprises a mechanism portion comprising a measurement bed on which a measurement subject lies in a lying state, a base provided on a side of one side face of the measurement bed, a measuring direction support arm fixed to the base movable in a measuring direction constituting a longitudinal direction of the measurement bed, a parallel support arm fixed to the measuring direction support arm and configured to be movable in a direction orthogonal to the measuring direction, a vertical support arm fixed to the parallel support arm and configured to be movable in an up and down direction, and a probe pivotably fixed to a front end of the vertical support arm for detecting amounts of detaching from reference positions in X, Y, Z, θ directions by pinching a probe provided at a front end of a scanning arm capable of moving in a longitudinal direction (X axis direction), a width direction (Y axis direction), a thickness direction (Z axis direction), a circumflex direction (twist angle θ centering on X axis) of the spinal column of the measurement subject on the measurement bed between the second finger and the third finger of a measuring person and three-dimensionally moving front ends of the fingers in a state of moving the front ends of the fingers from a position of the first cervical vertebra or a position of the first thoracic vertebra to a position of the fifth lumber vertebra of the spinal column of the measurement subject to output as detaching amount measuring data, an input apparatus for inputting a gender and height data of the measurement subject, and an image processing apparatus for inputting the detaching amount measuring data from the spinal column measuring apparatus, inputting the gender and height data of the measurement subject from the input apparatus, and generating a three-dimensional spinal column image of the measurement subject based on the detaching amount measuring data and the gender and height data of the measurement subject to provide to a display apparatus, wherein the image processing apparatus comprises converting means for converting the detaching amount measuring data in the X axis direction, the Y axis direction, the Z axis direction, the θ direction inputted from the measuring mechanism to convert to a predetermined provided data to be stored to converted data storing means, a basic diagram data base stored with an average size by the gender and height of the measurement subject and a basic shape thereof with regard to the respective vertebrae constituting the spinal column of the human body, data selecting means for selecting to input the respective vertebrae in correspondence with the gender and height data from the basic diagram data base in accordance with the gender and height data of the measurement subject inputted by the input apparatus to store to a vertebrae table, synthesizing means for generating an image of a total of the spinal column constituting a base based on sizes and shapes of the respective vertebrae stored to the vertebrae table, and an image data generating means for generating a three-dimensional spinal column image of the measurement subject at positions of coordinates in the X direction, the Y direction, the Z direction, the θ direction of the respective vertebrae based on an image of a total of the spinal column generated by the synthesizing means and the converted data stored to the converted data storing means, wherein the three-dimensional spinal column image of the measurement subject is generated into a displayable display data by being moved in a predetermined direction or rotated by a predetermined angle to be able to be outputted based on a predetermined instruction, wherein the measuring direction support arm comprises a moving mechanism comprising a rail fixed to the base and a slider movably fixed onto the rail, an attaching seat for attaching to fix the parallel support arm, a pivoting mechanism interposed between the slider of the moving mechanism and the attaching seat for making the attaching seat pivotable in a vertical face, a pivoting mechanism interposed between the slider of the moving mechanism and the attaching seat for making the attaching seat pivotable in a horizontal face, or a horizontal slide mechanism interposed between the slider of the moving mechanism and the attaching seat for making the attaching seat movable in a horizontal direction.

In order to achieve the above-described and other objects, a human spinal column measuring and displaying system according to the present invention comprises a spinal column measuring apparatus comprising a mechanism portion comprising a measurement bed on which a measurement subject lies in a lying state, a base provided on a side of one side face of the measurement bed, a measuring direction support arm fixed to the base movable in a measuring direction constituting a longitudinal direction of the measurement bed, a parallel support arm fixed to the measuring direction support arm and configured to be movable in a direction orthogonal to the measuring direction, a vertical support arm fixed to the parallel support arm and configured to be movable in an up and down direction, and a probe pivotably fixed to a front end of the vertical support arm for detecting amounts of detaching from reference positions in X, Y, Z, θ directions by pinching a probe provided at a front end of a scanning arm capable of moving in a longitudinal direction (X axis direction), a width direction (Y axis direction), a thickness direction (Z axis direction), a circumflex direction (twist angle θ centering on X axis) of the spinal column of the measurement subject on the measurement bed between the second finger and the third finger of a measuring person and three-dimensionally moving front ends of the fingers in a state of moving the front ends of the fingers from a position of the first cervical vertebra or a position of the first thoracic vertebra to a position of the fifth lumber vertebra of the spinal column of the measurement subject to output as detaching amount measuring data, an input apparatus for inputting a gender and height data of the measurement subject, and an image processing apparatus for inputting the detaching amount measuring data from the spinal column measuring apparatus, inputting the gender and height data of the measurement subject from the input apparatus, and generating a three-dimensional spinal column image of the measurement subject based on the detaching amount measuring data and the gender and height data of the measurement subject to provide to a display apparatus, wherein the image processing apparatus comprises converting means for converting the detaching amount measuring data in the X axis direction, the Y axis direction, the Z axis direction, the θ direction inputted from the measuring mechanism to convert to a predetermined provided data to be stored to converted data storing means, a basic diagram data base stored with an average size by the gender and height of the measurement subject and a basic shape thereof with regard to the respective vertebrae constituting the spinal column of the human body, data selecting means for selecting to input the respective vertebrae in correspondence with the gender and height data from the basic diagram data base in accordance with the gender and height data of the measurement subject inputted by the input apparatus to store to a vertebrae table, synthesizing means for generating an image of a total of the spinal column constituting a base based on sizes and shapes of the respective vertebrae stored to the vertebrae table, and an image data generating means for generating a three-dimensional spinal column image of the measurement subject at positions of coordinates in the X direction, the Y direction, the Z direction, the θ direction of the respective vertebrae based on an image of a total of the spinal column generated by the synthesizing means and the converted data stored to the converted data storing means, wherein the three-dimensional spinal column image of the measurement subject is generated into a displayable display data by being moved in a predetermined direction or rotated by a predetermined angle to be able to be outputted based on a predetermined instruction, wherein the measurement bed is constituted by a base portion installed on a floor, a fixed base fixed onto the base portion, and a movable mechanism comprising a moving base horizontally movable on the fixed base, a bed sheet portion fixed onto the moving base of the movable mechanism.

ADVANTAGE OF THE INVENTION

According to the human spinal column measuring and displaying system according to the invention described in Claim 1, the accurate three-dimensional image pseudonymously formed with "in what state the spinal column is bent" can be displayed by a simple method of scanning the probe on the spinal column of the lying down measurement subject from a surface thereof, and a state of the spinal column can optically be confirmed.

Thereby, the operator can easily make the measurement subject understood by explaining "to what degree the spinal column is bent" before treatment and after treatment while showing the image.

Further, a patient constituting the measurement subject can optically confirm a state of the spinal column similar to actual not by specialized medical terms but as the image, and therefore, the patient can easily understand "how and to which direction what portion of the spinal column of the patient per se is bent".

BRIEF DESCRIPTION OF THE DRAWINGS

FIG. 7 illustrates views of a table of the vertebrae showing average measured values of the vertebrae.

FIG. 11 illustrates views showing images of the spinal column by measuring the spinal column by a spinal column measuring apparatus, and generating the images by an image processing apparatus based on the measured data to be displayed on a display apparatus according to the human spinal column measuring and displaying system according to the invention.

FIG. 12 illustrates images of the spinal column generating to display the lumbar vertebra, the thoracic vertebra in the spinal column displayed by FIG. 11.

Figure 1:
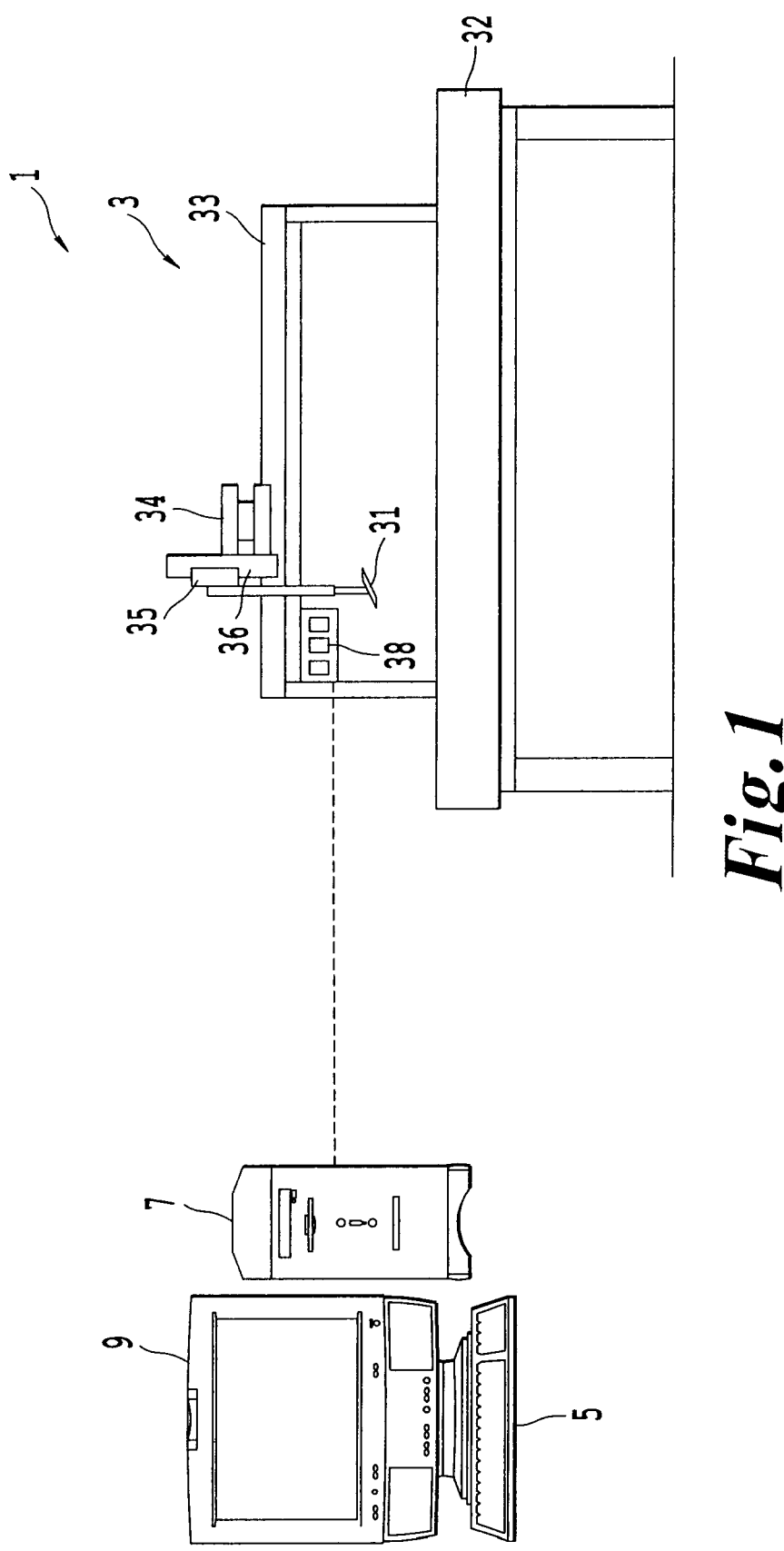
FIG. 1 is an outline constitution view of a human spinal column measuring and displaying system according to an embodiment of the invention.

DESCRIPTION OF REFERENCE NUMERALS AND SIGNS 1. human spinal column measuring and displaying system
3. spinal column measuring apparatus
5. input apparatus
7. image processing apparatus
9. display apparatus
31. probe
31$a$. moving mechanism
31$b$. attaching seat
31$c$. pivoting mechanism
32. measurement bed
34. measuring direction support arm
35. parallel support arm
36. vertical support arm 38. coordinate detecting system
71. central processing unit (CPU)
72. read only memory (ROM)
73. main memory (RAM)
74. hard disk apparatus
71a. converting means
71b. data selecting means
71c. synthesizing means
71d. image data generating means
73a. converted data storing portion
73b. image data storing portion
74c. measured data storing means
74d. basic diagram data base
74e. vertebrae table

BEST MODE FOR CARRYING OUT THE INVENTION

An embodiment of the invention will be explained in reference to the drawings as follows.

FIG. 1 is an outline view of a human spinal column measuring and displaying system according to the invention. In FIG. 1 in gross classification, a human spinal column measuring and displaying system 1 according to the invention is constituted by a spinal column measuring apparatus 3 capable of measuring bending of the spinal column of the human body as a measured data of an amount of detaching from a reference value, an input apparatus 5 for inputting gender, height data of the measurement subject, an image processing apparatus 7 for inputting the detaching amount measured data from the spinal column measuring apparatus 3 and a data from the input apparatus 5 and generating a three-dimensional spinal column image of the measurement subject based on the detaching amount measured data and the gender, height data of the measurement subject, and a display apparatus 9 for displaying an image data from the image processing 7.

Here, the spinal column measuring apparatus 3 will further be explained. The spinal measuring apparatus 3 is a measuring apparatus for detecting amounts of detaching from reference positions in X, Y, Z, θ directions by pinching a probe 31 provided at a front end of a scanning arm freely moving in a longitudinal direction (X axis direction), a width direction (Y axis direction), a thickness (Z axis direction), a circumflexing direction (a twist angle θ centering on X axis) of the spinal column of a measurement subject between the second finger and the third finger of a measuring person and three-dimensionally moving the finger tip from a position of the first cervical vertebra or a position of the first thoracic vertebra to a position of the sacral vertebra of the spinal column of the measurement subject lying down on a measurement bed 32 in a state of moving the finger tip in line therewith.

Explaining further, the spinal column measuring apparatus 3 includes the measurement bed 32 on which the measurement subject lies in a state of lying down, a base 33 fixed to one side face side of the measurement base 32 to be installed vertically, a measuring direction support arm 34 fixed to the base 33 movably in a left and right direction (X direction) of the drawing, a parallel support arm 35 fixed to the measuring direction support arm 34 and made to be movable in a vertical direction (Y axis direction) of the drawing, a vertical support arm 36 fixed to the parallel support arm 35 and made to be movable in an up and down direction (Z axis direction) of the drawing, the probe 31 pivotably fixed to a front end of the vertical support arm 36, an X axis detector (not illustrated) capable of detecting an amount of moving the measuring direction support arm 34, a Y axis detector (not illustrated) capable of detecting an amount of moving an amount of moving the parallel support arm 35, a z axis detector (not illustrated) capable of detecting an amount of moving the vertical support arm 36, an angle detector (not illustrated in FIG. 1) capable of measuring an amount of pivoting the probe 31 as an angle θ, and a coordinate detecting system 38 constituting data of coordinates based on detected data from the X axis detector, the Y axis detector, the Z axis detector and the angle detector.

Figure 2:
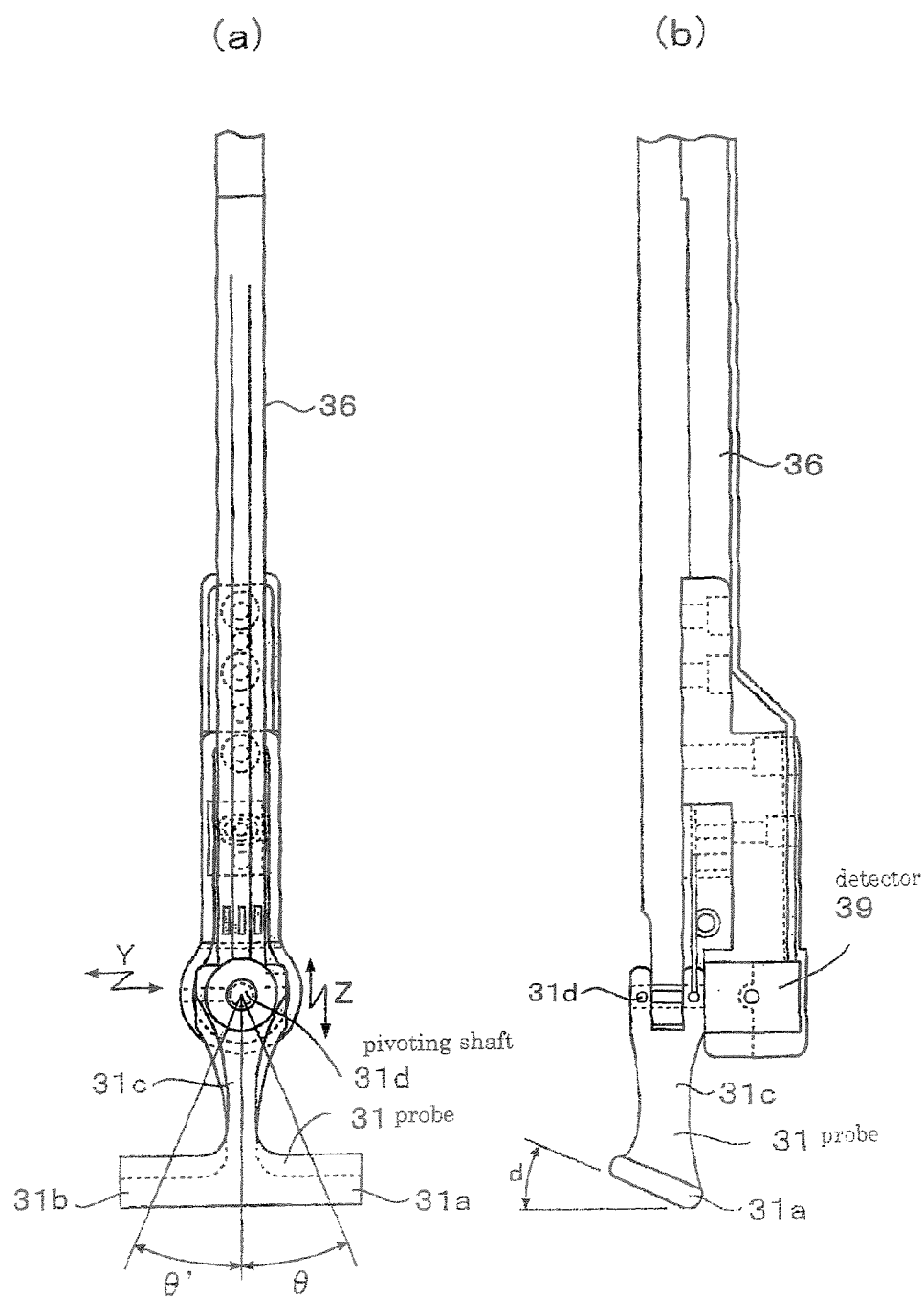
FIG. 2 illustrates detailed constitution views of a vicinity of a probe used in the human spiral column measuring and displaying system according to the embodiment of the invention.

FIG. 2 illustrates detailed constitution views of a vicinity of a probe used in the human spinal column measuring and displaying system according to the embodiment of the invention, FIG. 2(a) is a front view, FIG. 2(b) is a side view.

In FIG. 2(a) and FIG. 2(b), the probe 31 is for scanning the spinal column of a patient (measurement subject) from above a surface thereof. As shown by FIG. 2(a), the probe 31 is constituted by grasping pieces 31a, 31b, a fixed piece 31c formed by a predetermined length in a vertical direction at a center portion of the grasping pieces 31a, 31b. According to the probe 31, as shown by FIG. 2(a), FIG. 2(b), the fixed piece 31c is pivotably fixed to a lower end of the vertical support arm 36 by a rotating shaft 31d, thereby, formed in an inverse T-like shape. As shown by FIG. 2(b), the grasping pieces 31a, 31b of the probe 31 are formed by a shape having an angle of α relative to an advancing direction of scanning along the spinal column. Further, an angle detector 39 is provided at a vicinity of the rotating shaft 31d of the probe 31 of the vertical support arm 36 to be able to measure twist angle θ, θ' to be outputted as angle measuring data as shown by FIG. 2(a).

Further, the spinal measuring apparatus 3 is made to be able to measure by contact a state of bending the spinal column in accordance with amounts of moving the measuring direction support arm 34, the parallel support arm 35, the vertical support arm 36 (detaching amounts) and an amount of rotating the probe 31 centering on the rotating shaft 31d by pinching the grasping pieces 31a, 31b of the probe 3 between the second finger and the third finger of the measuring person and moving (scanning) the tips of the second finger and the third finger from the first cervical vertebra position or the first thoracic vertebra position (root of neck) to the sacral vertebra position of the measurement object lying down on the measurement bed 32.

Further, the measurement bed 32 is constituted by a size of a width of about 800 m, a length of about 1800 mm, a height of about 500 mm by which the patient (measurement subject) can lie down. By making the patient (measurement subject) lie down at a predetermined position of the measurement bed 32, the spinal column of the patient (measurement subject) is brought into a constant state to be able to accurately measure the spinal column when the probe 31 is scanned on the spinal column.

That is the measurement bed constituted such that in measuring the bent state of the spinal column of the patient (measurement subject) lying down on the measurement bed 32, when the measuring person holds the probe 31 by the hand to move from the neck in the waist direction on the surface of the spinal column, the probe 31 follows recesses and projections and shifts in the left and right direction within a range of, for example, 900 [mm] in X direction, 400 [mm] in Y direction, 200 [mm] in Z direction by the measuring direction support arm 34, the parallel support arm 35, the vertical support arm 36.

Further, according to the embodiment, the coordinate detecting system 38 is attached to the base 33 and counts amounts of moving the probe 3 in X direction, Y direction, Z direction as predetermined pulse signals by, for example, an encoder (24 bits up down counter board (PCN24-4(PCI)) and detects values of coordinates when the coordinate values coincide with count comparison values arbitrarily set for the respective coordinates as digital values. Further, the coordinate detecting system 38 is made to be able to transmit the measured value to the image processing apparatus 7.

Further, the image processing apparatus 7 is connected with the spinal column measuring apparatus 3 by a cable to be able to supply the measured data from the spinal column measuring apparatus 3 to the image processing apparatus 7 by way of the cable. Further, the image processing apparatus 7 is electrically connected with the input apparatus 5 the display apparatus 9, the image processing apparatus 7 can be inputted with necessary data from the input apparatus 5, further, is constituted to be able to display a result processed by the image processing apparatus 7 or the like by the display apparatus 9.

Figure 3:
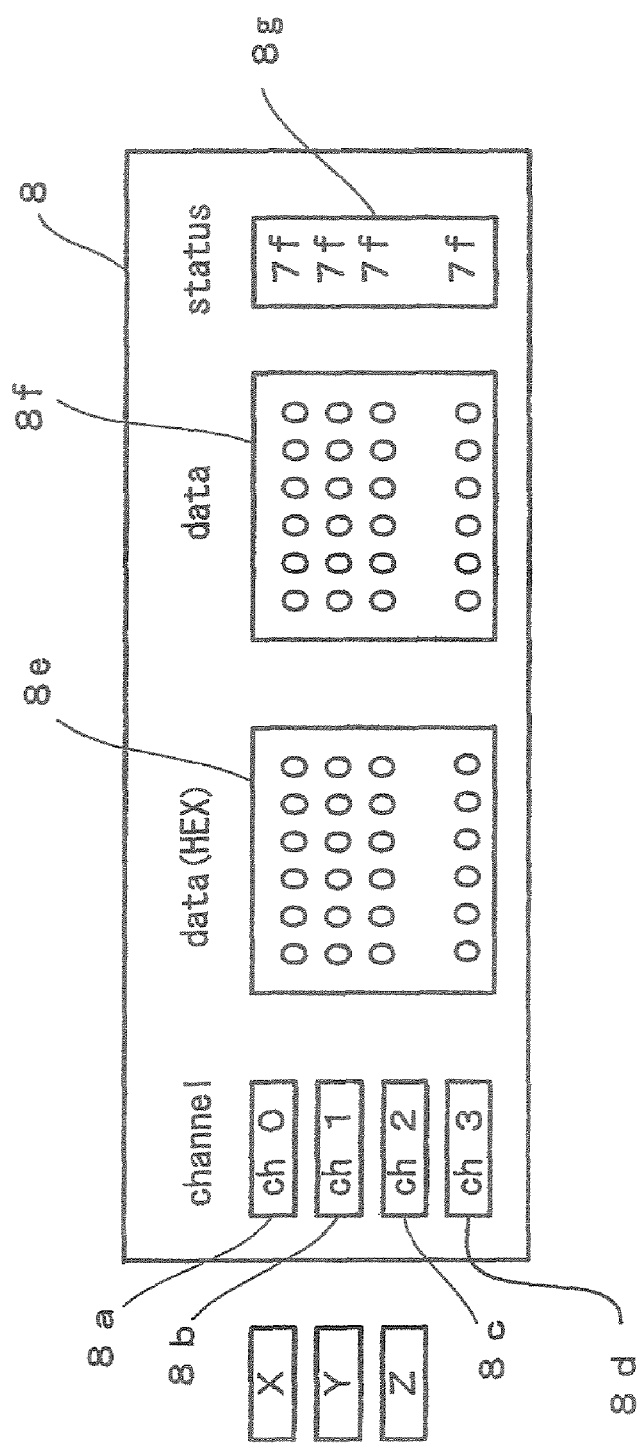
FIG. 3 is an explanatory view of a coordinate detecting system used in the human spinal column measuring and displaying system according to the invention.

FIG. 3 is an explanatory view of a coordinates detecting system used in the human spinal column measuring and displaying system according to the invention. In FIG. 3, the coordinates detecting system 38 includes respective channels (ch0, ch1, ch2, ch3) 38a, 38b, 38c, 38d of X coordinate axis, Y coordinate axis Z coordinate axis, and the angle θ, a hexadecimal display portion 38e for detecting and displaying hexadecimal data, a decimal display portion 38f for detecting and displaying decimal data, and a status display portion 38g for displaying count values of coordinate values at each 0.1 second and a predetermined angle value as a status.

Figure 4:
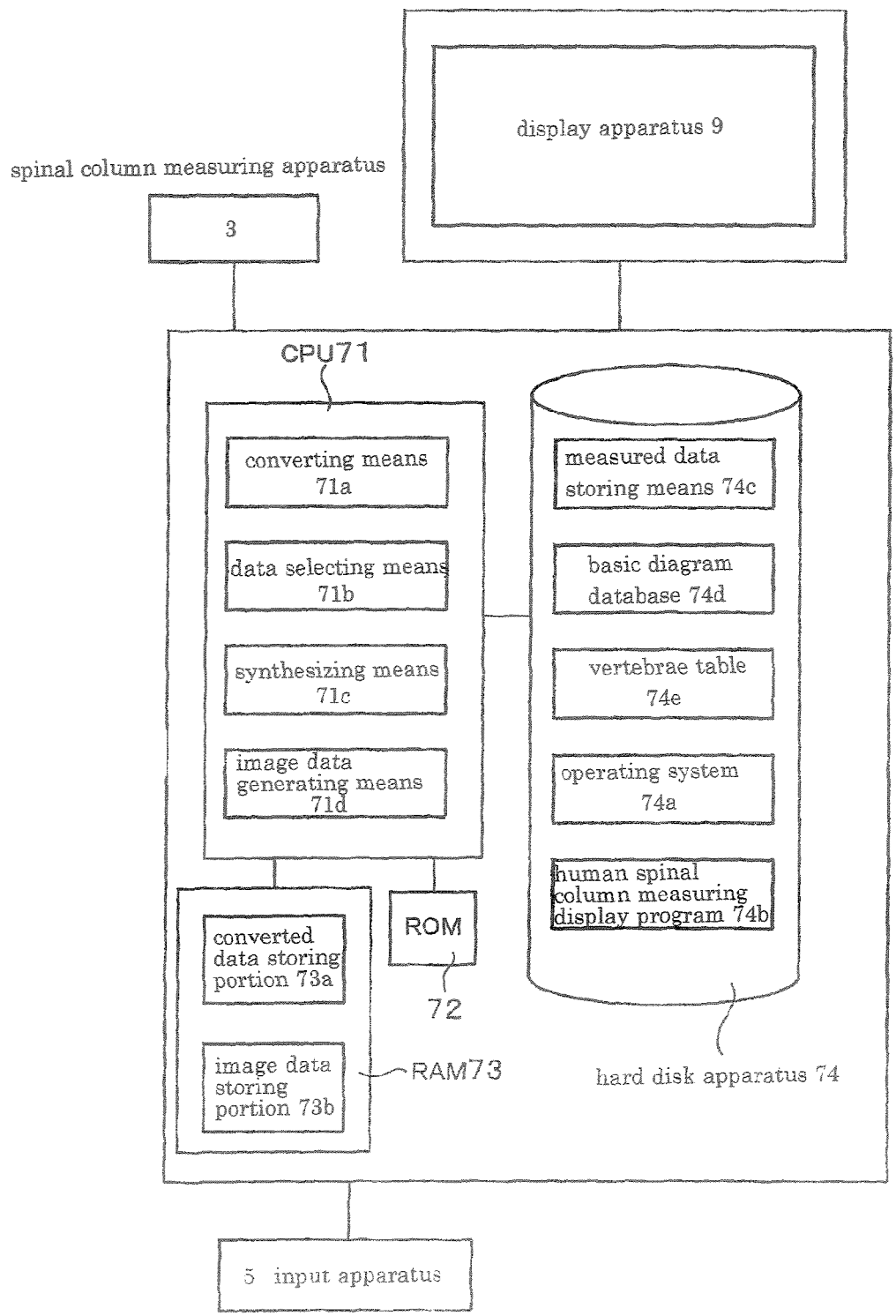
FIG. 4 is a block diagram showing an image processing apparatus used in the human spinal column measuring and displaying system.

FIG. 4 is a block diagram showing an image processing apparatus used in the human spinal column measuring and displaying system of the invention.

In FIG. 4 according to the embodiment, the image processing apparatus 7 is, for example, a personal computer for carrying out a predetermined operation based on the measured data transmission from the spinal column measuring apparatus 3 and forming an image data for displaying a state of the spinal column in a real mode.

For example, as the image processing apparatus 7, according to the embodiment, PowerMac 7100/66AV of Apple cooperation is used as a personal computer. The image processing apparatus 7 comprising the personal computer includes a central processing unit (CPU) 71 for executing various operational processings and programs, a read only memory (ROM) 72 for executing a basic operation in starting or the like a main memory (RAM) 73 having an area for storing an operating system and a human spinal column measuring and displaying program for executing processings of the invention, and a data storing area necessary for other processings a hard disk apparatus 74 for storing the operating system and the human spinal column measuring and displaying processing program for executing processings of the invention and a database necessary in executing the human spinal column measuring and displaying processing program and other input/output board and a power source apparatus.

Further, according to the image processing system 7 comprising the personal computer, when the power source is inputted, CPU 71 executes programs of ROM 72, the operating system is stored from the hard disk apparatus 74 to the predetermined area of RAM 73, at a time point at which storing to RAM 73 has been finished, CPU 71 executes the operating system of RAM 73 and a usable state (basic screen) is displayed on the display apparatus 9 to be brought into a standby state. At this occasion, when, for example, the image processing apparatus 7 is instructed to start the human spinal column measuring and displaying program by using the input apparatus 5 and the display apparatus 9, or the image processing apparatus 7 is set to automatic starting, the image processing apparatus 7 outputs the human spinal column measuring and displaying program from the hard disk apparatus 74 to be stored to RAM 73, thereafter, by executing the human spinal column measuring and displaying program stored to RAM 73 by CPU 71, as shown by FIG. 4, converting means 71a, data selecting means 71b, synthesizing means 71c and image data generating means 71d are realized.

Further, as shown by FIG. 4, the hard disk apparatus 74 is stored with an operating system 74a, a human spinal column measuring and displaying program 74b, measuring data storing means 74c for storing a measured data of a digital value from the coordinates detecting apparatus 38, a basic diagram data base 74d stored with image data of a basic model of the vertebrae, the vertebrae table data base 74e which is referred to when a spinal column image is formed by the converted data.

Further, RAM 73 is provided with a converted data storing portion 73a and an image data storing portion 73b when the human spinal column measuring and displaying program is executed in CPU 71.

Further, the converting means 71a realized by CPU 71 is means for converting the measured data stored to the measured data storing means 74c by a predetermined conversion procedure. Further, the synthesizing means 71b realized by CPU 71 is means for forming an image of the vertebrae of the measured person based on the converted data. The image data generating means 71c realized by CPU 71 is means for synthesizing the respective vertebrae generated by the synthesizing means 71b to be stored to the image data storing portion 73b.

The input apparatus 5 is a keyboard or a mouse for inputting data of gender height or the like of the subject for measuring the vertebrae.

According to the embodiment, the display apparatus 9 is a CRT display apparatus or a liquid crystal display apparatus and is apparatus for displaying an image in a real mode by image data of the state of the vertebrae generated by the image processing apparatus 7 and stored to the image data storing portion 73b.

That is, according to the spinal column measuring apparatus 3, when the probe 31 is pinched by the fingers, and the fingers are moved from the head portion to the waist portion of the human body along the spinal column of the human body constituting the object of the measurement, a measured amount in X axis direction can be provided, when the probe 31 is moved in a width direction of the human body along "bending" or the like of the spinal column of the human body, a measured amount in Y axis direction can be provided, when the probe 31 is moved in a direction of moving up and down the probe 31 along recesses and projections of the spinal column of the human body, a moved amount in Z axis direction can be provided, further, by pivoting the probe 31 centering on the rotating shaft 31d, the circumflex amount θ can be provided.

Figure 5:
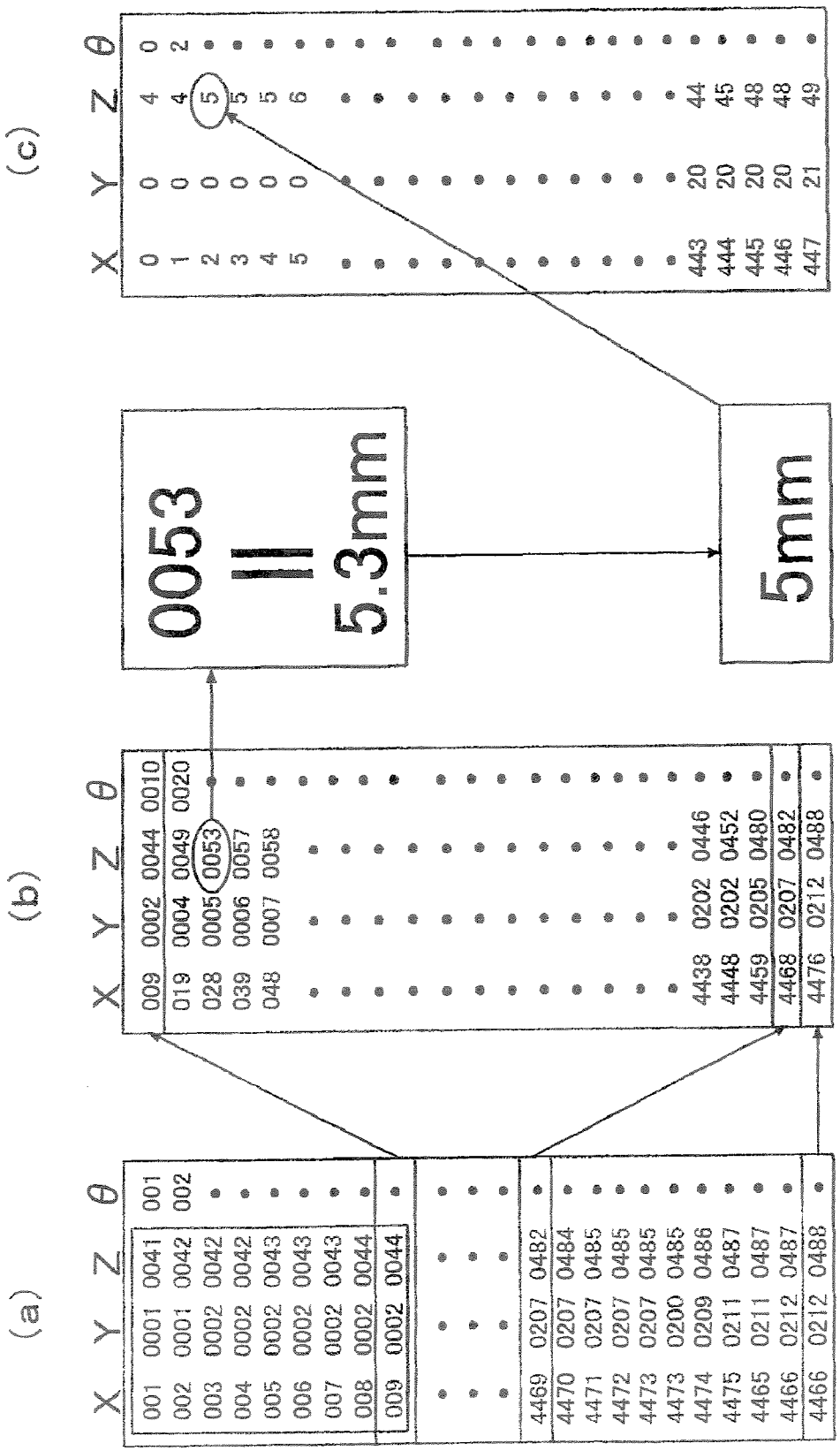
FIG. 5 illustrates explanatory views of a behavior of converting a measured data into a converted data by converting means in the human spinal column measuring and displaying system according to the invention.

FIG. 5 illustrates views for explaining a behavior of converting the measured data into the converted data by the converting means in the human spinal column measuring and displaying system according to the invention.

That is, FIG. 5(a) shows a measured data stored to the measured data storing means 74a and is a measured data of X direction, Y direction, Z direction, the angle θ respectively from left. By dividing X direction (length direction of the spinal column) for each 1 mm by the converting means 71a, there are detected "009" which is a maximum coordinate value in X direction from "001" to "009", "019" which is a maximum value thereof from "011" to "019", . . . , "4469" which is a maximum thereof from "4461" to "4469" and a final data "4476", that is, values in X direction of "009"

"019" . . . , "4469", "4476", and the coordinate values in X directions Y direction and Z direction are temporarily stored to a memory (RAM) or the like FIG. 5(b) shows a behavior of storing the coordinate values to the memory (RAM 73).

The measured data detected in this way is a numeral value a lower first value of which is equal to or smaller than a decimal point and since an error in measurement is conceivable to includes an integer is provided by rounding down numbers below the decimal point.

Further, as shown by FIG. 5(b), a coordinate value in X direction, a coordinate value in Y direction, a coordinate value in Z direction, and a coordinate value of the angle θ constituting initial measured data are (X, Y, Z, θ)=(009, 0002, 0044, 0008). The converting means 71a carries out an operation of rounding down numerals below the decimal point of the measured data, for example, as follows. That is, the converting means 71a sets the coordinate values to (X, Y, Z, θ)=(0, 0, 4, 0). Next, with regard to (X, Y, Z, θ) (019, 0004, 0049, 0001), the converting means 71a converts the coordinate values to (X, Y, Z, θ)=(1, 0, 4, 0). Successively, with regard to (X, Y, Z, θ)=(029, 3005, 0053, 0013), the converting means 71a converts the coordinate values to (X, Y, Z, θ)=(2, 0, 5, 1), and with regard to the final measured data (X, Y, Z, θ)=(4476, 0212, 0488, 0030), the coordinate values are converted to (X, Y, Z, θ)=(447, 21, 48, 3), thereby, numeral values respectively converted into integers can be provided as shown by FIG. 5(c).

Further, the numerals converted by the converting means 71a are stored to the converted data storing means 73a as converted data based on the measured data.

Meanwhile, since a number of the vertebrae constituting the spinal column of the human body is determined, the length of the spinal column is changed by a height difference or the like, and therefore an average measured value data constituting the base is previously stored as the vertebrae table 74c. Further, the shape of the vertebrae is stored to the basic diagram data base 74d as a basic model.

Further, in correspondence with the gender, height data of the measurement subject inputted from the inputting means 7, the data selecting means 71b selects output the respective vertebrae in correspondence with the gender, height data from the basic diagram data base 74d is stored to the vertebrae table 74e.

The synthesizing means 71c generates an image of a total of the spinal column constituting the base, based on sizes, shapes of the respective vertebrae stored to the vertebrae table 74e.

Further, the image data generating means 71d can carry out a simulation of the spinal column of the measurement subject by generating a three-dimensional spinal column image of the measurement subject at coordinate positions of X direction, Y direction, Z direction, θ direction of the respective vertebrae by reflecting the converted data stored to the converted data storing means 73a to an image of a total of the vertebrae generated by the synthesizing means 71c. By transmitting the image data of the spinal column of the measurement subject generated by the image data generating means 71d to the display apparatus 9, a pseudo-spinal column is displayed on the display apparatus 9 as an image in a real mode, and it can be known which vertebra is a portion at which the spinal column is bent.

The basic diagram database 74d is stored with data of the vertebrae (spinal column) of the human body. The data of the vertebrae (spinal column) of the human body is an image data comprising the cervical vertebrae (7 pieces) the thoracic vertebrae (12 pieces), the lumber vertebrae (5 pieces), the sacral vertebrae (5 pieces), the coccyges vertebrae (5 pieces) constituting the vertebrae (spinal column) of the human body showing shapes of the vertebrae. According to the basic structure of the vertebrae, the vertebrae are contiguous to each other by interposing the inter vertebral disks on the belly side, having clearances (the vertebra holes) passing the spinal cord and surrounded by the bones on the back side, and having thorn projections on the rear side.

Figure 6:
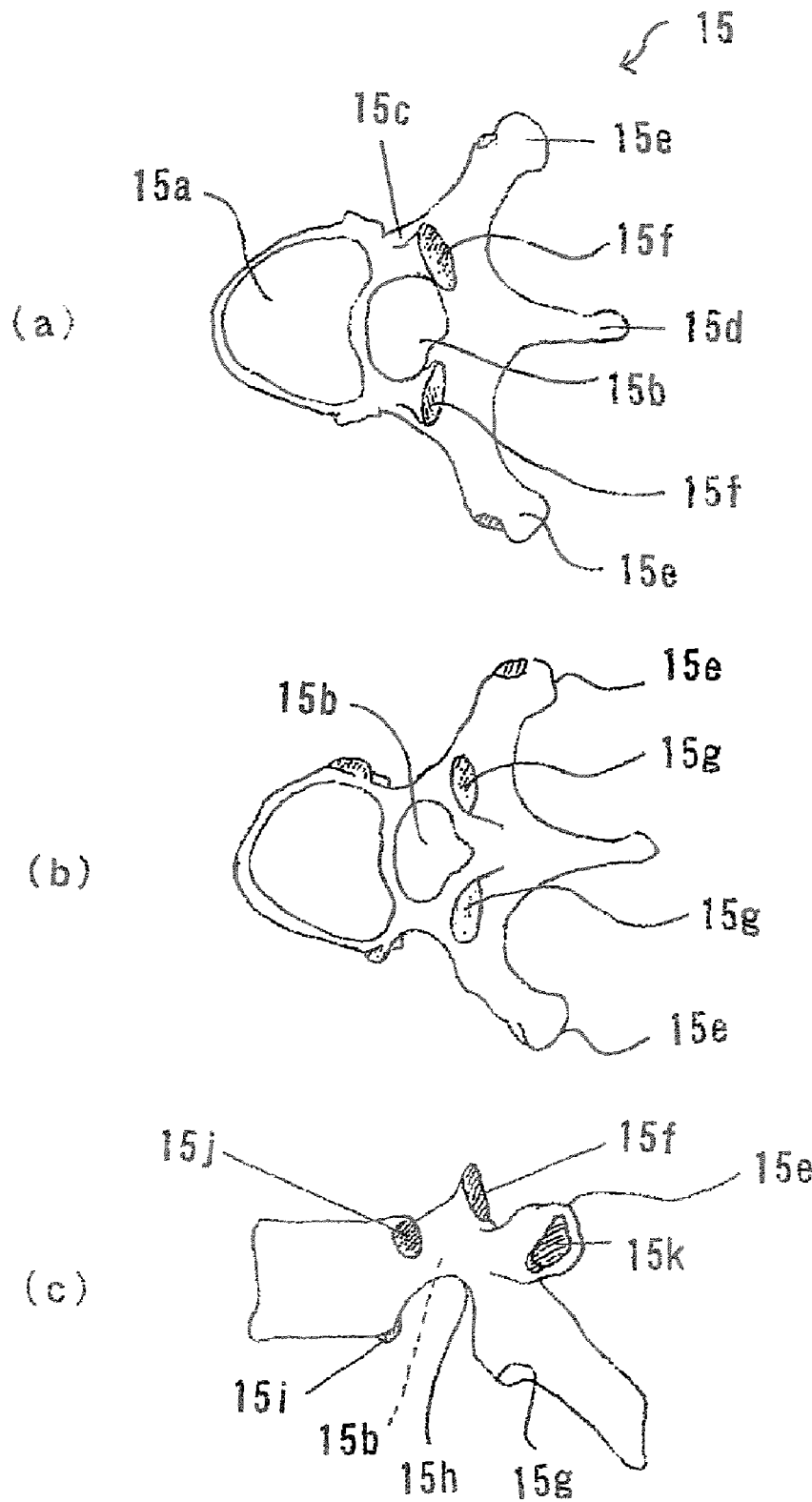
FIG. 6 illustrates explanatory views of a basic structure of the vertebra (the fourth thoracic vertebra) constituting the spinal column (the vertebrae).

FIG. 6 illustrates explanatory views of the basic structure of the vertebra (the fourth thoracic vertebra) constituting the vertebrae (spinal column).

Here, FIG. 6(a) shows a shape of an upper face of the vertebra 15 comprising by respectively forming the vertebra body 15a which is rounded, the vertebra hole 15b on the back side, lamina roots 15c on both side portions of the vertebra hole 15b, the thorn projection 15d at the center of the rear back side, the lateral projections 15e at both side portions thereof, and forming the upper joint projections 15f continuous to the other vertebra on skewed upper sides (back side direction) on both side portions of the vertebra hole 15b.

FIG. 6(b) shows a shape of a lower face of the vertebra 15 and constituted by forming the lower joint projections 15g continuous to the other vertebra on skewed lower sides (directions from back side to the belly side) on both side portions of the vertebra hole 15b.

FIG. 6(c) shows a shape of a left side face of the vertebra 15 which is formed by the vertebra cut marks 15h chipped off in a semicircular shape on the lower side of the vertebra hole 15b, the lower rib cavities 15i on both lower sides on the belly side of the lower vertebra cutting marks 15h, the upper rib cavities 15j on both upper sides of the lower rib cavities, and the laterally projected rib cavities 15k at front end portions of the lateral projection 15e.

Further, the image data of the respective vertebrae constituting such shapes are stored to the basic diagram data base 74a.

According to the embodiment, the vertebrae table 74e is constituted by tabulating, for example, average measured values (±standard deviations) of the vertebrae of a Japanese adult male person and average measured values (±standard deviations) of the vertebrae of a Japanese adult female person.

FIG. 7 shows the average measured values of the vertebrae as the vertebrae table 74e, FIG. 7(a) shows measured values of the vertebrae of a Japanese adult male person (age: 26 years) for example, average values (±standard deviations) of the belly side heights thereof are 12.93 [mm]±1.45 [mm] for the third cervical vertebra, 12.24 [mm]±1.21 [mm] for the fourth cervical vertebra, . . . , 15.12 [mm]±1.12 [mm] for the first thoracic vertebra, . . . , 22.33 [mm]±1.91 [mm] for the twelfth thoracic vertebra, 23.39 [mm]±1.80 [mm] for the first lumber vertebra, . . . , 25.15 [mm]±2.29 [mm] for the fifth lumber vertebra, showing respectives of back side heights, upper face arrow mark diameters, lower face arrow mark diameters, upper face lateral diameters, lower face lateral diameters for the third cervical vertebra through the fifth lumber vertebra.

FIG. 7(b) shows average measured values of the vertebrae of a Japanese adult female person (age: 26 years), similarly, average values (±standard deviations) of the belly side heights thereof are 12.28 [mm]±1.23 [mm] for the third cervical vertebra, 11.61 [mm]±1.17 [mm] for the fourth cervical vertebra, . . . , 14.89 [mm]±1.23 [mm] for the first thoracic vertebra, . . . , 22.10 [mm]±1.80 [mm] for the twelfth thoracic vertebra, 23.76 [mm]±1.94 [mm] for the first lumber vertebra, . . . , 24.85 [mm]±2.11 [mm] for the fifth lumber vertebra, showing respectives of back side heights, upper face arrow mark diameters, lower face arrow mark diameters, upper face lateral diameters, lower face lateral diameters for the third cervical vertebra through the fifth lumber vertebra.

Further, the vertebrae table 74e is formed for respective male and female persons and stored to the predetermined storing area of the hard disk apparatus 74.

The synthesizing means 71c provides a pseudo-image of the spinal column in a real mode by reflecting sizes in accordance with the vertebrae table 16 to images of shapes of the respective vertebrae stored to the basic diagram database 74d. That is among the respective vertebrae stored to the basic diagram data 15, for example, the third thoracic vertebra is disposed on the upper side of the fourth thoracic vertebra by interposing the intervertebral disk, and the upper joint projection 15f of the fourth thoracic vertebra and the lower joint projection 15g of the third thoracic vertebra are continuous. Further, when the first cervical vertebra through the coccygeal vertebra are successively synthesized such that the second thoracic vertebra is disposed on the upper side of the third thoracic vertebra and the first thoracic vertebra is disposed on the upper side an image of the spinal column is formed.

That is, a data stored to the vertebrae table 74e is constituted by average values of Japanese by taking into account standard deviations, and based on the gender and the height, by sizes of 18 pieces of the vertebrae from the first thoracic vertebrae at a start of measurement to the fifth lumber vertebra (actual display is 15 pieces of the first cervical vertebra through the sacral vertebra), the basic diagram database 74d is selected to combine to provide the image of the spinal column of the basis model.

As has already been explained, the image data generating means 71d generates an image data of a state of the spinal column of the individual measurement subject by reflecting the converted data (measured data) to the shape of the spinal column constituting the base formed by the synthesizing means 71c.

That is, as described above, in the converted data (measured data), for each 1 [mm] in X direction which is a longitudinal direction of the spinal column, positions in Y direction which is the width direction of the back, Z direction which is the thickness direction of the breast are measured and the converted data (measured data) are divided to allocate to the respective vertebrae. Then, predetermined that what mm to what mm of X values correspond to "the number×lumber vertebra".

Further, the image data of the spinal column can be displayed by rotating the image of the spinal column in a predetermined direction when the coordinates of the view point are changed by utilizing the above-described image processing software program of the three-dimensional computer graphics executed by CPU 71.

Figure 8A:
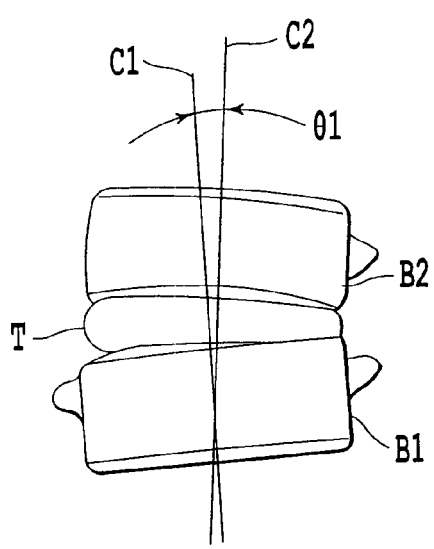
FIG. 8 illustrates explanatory views showing a behavior of calculating an angle between the vertebrae.
Figure 8B:
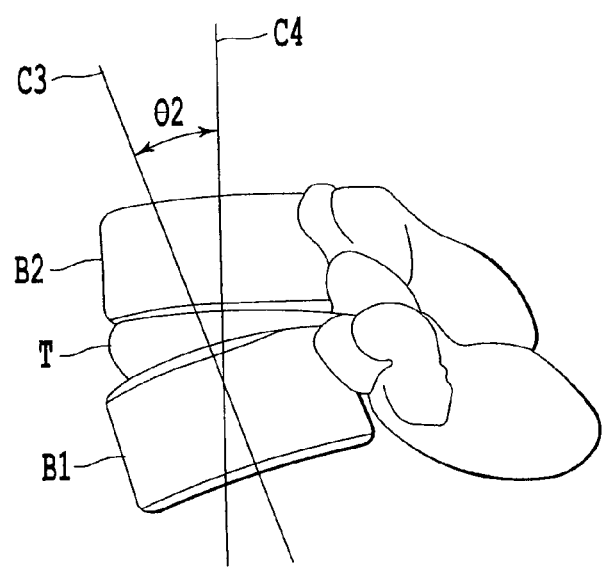

FIG. 8 illustrates explanatory views showing a behavior of calculating angles among the vertebrae, FIG. 8(a) is an explanatory view showing a bent angle in left and right directions between the vertebrae, FIG. 8(b) is an explanatory view showing a bent angle in front and rear direction therebetween.

When as shown by FIG. 8(a), for example, the third lumber vertebrae is designated by notation B1, the intervertebral disk is indicated by notation T, and the second lumber vertebra is designated by notation B2, the bent angle can be calculated from Y value in correspondence with the portion of the second lumber vertebra and Y value in correspondence with the portion of the third lumber vertebra of the converted data (measured data) divided into the respective vertebrae. That is, when the spinal column is not bent, since the spinal column is not inclined to either of left and right, all of Y value becomes "0", however, for example, when the second lumber vertebra is inclined to right, Y value is measured as "1" or "2" and when the second lumber vertebra is inclined to left, Y value is measured as "−1" or "−2".

When the converted data (measured data) is reflected to the basic model of the spinal column, it is calculated that there is brought about an inclination of an amount of an angle β1 between center C1 of the third lumber vertebra and center C2 of the second lumber vertebra and the image of the vertebrae is generated by deforming the intervertebral disk T.

Next, when as shown by FIG. 8(b), similar to the above-described, the third lumber vertebra is designated by notation B1, and the second lurker vertebra is designated by notation B2, the image of the vertebrae can be provided form Z value in correspondence with the portion of the third lumber vertebra of the converted data (measured data) divided to the respective vertebrae.

That is, in the case of the lumber vertebrae, when the second lumber vertebra (C4) is inclined relative to the third lumber vertebra (C3) to the back side by "9.27 degrees" in the basic model in which Z value is "−10" (according to the embodiment, with regard to a plane comprising X coordinates and Y coordinates, this side is indicated as plus and the depth side is indicated as minus) is normal, and in contrast thereto, when Z value of the converted data (measured data) is "−7", an inclination β2 between C3 and C4 is calculated as, for example, "5.06 degrees".

Next, twist of the spinal column will be explained.

Figure 9:
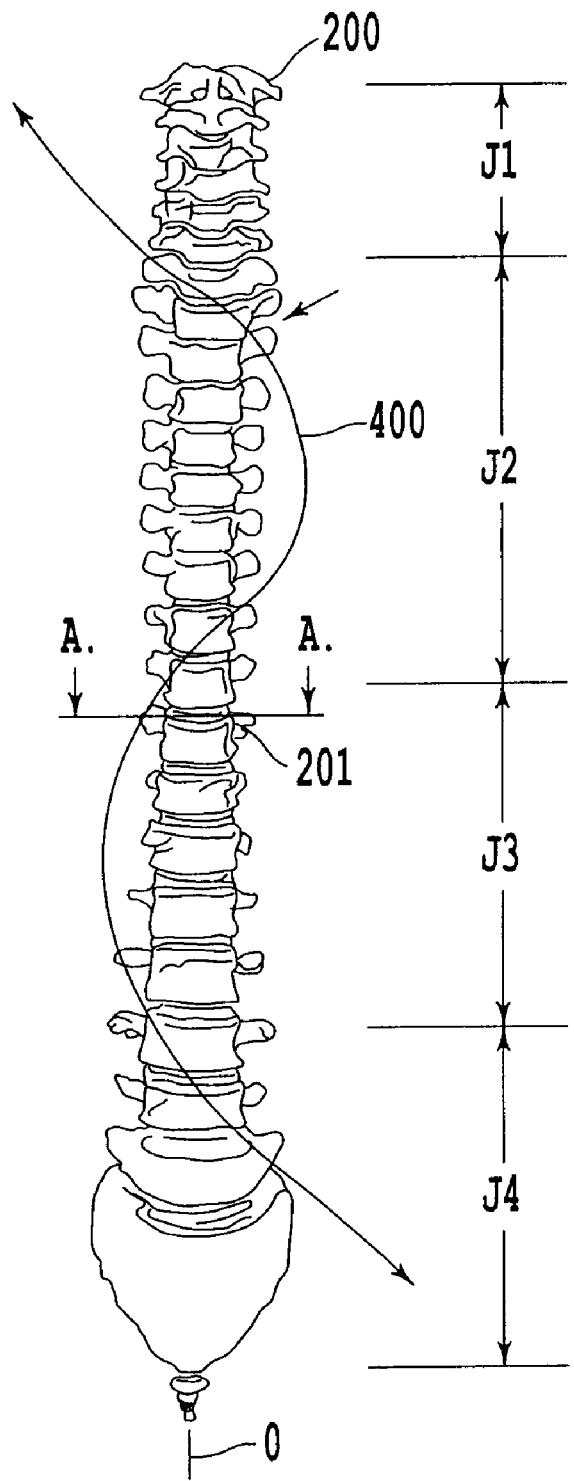
FIG. 9 is an explanatory view showing a total picture of the spinal column.
Figure 10:
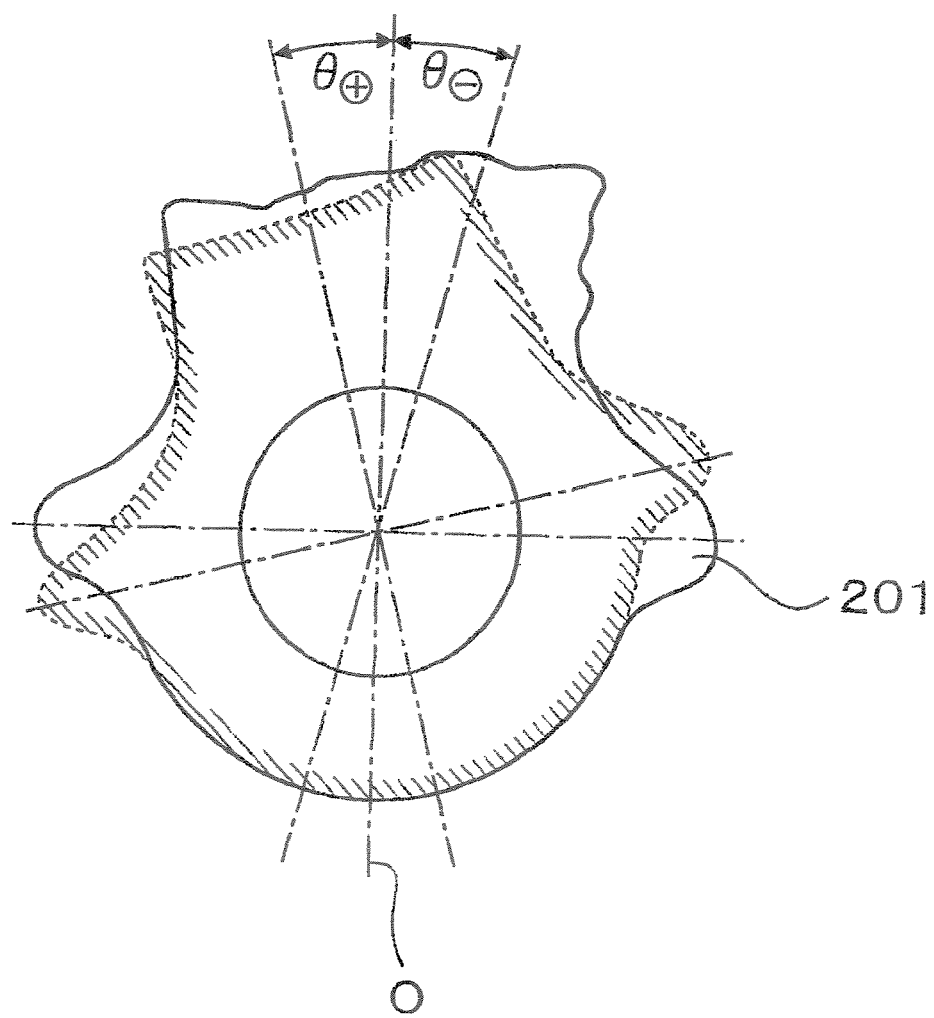
FIG. 10 is a sectional view taken along a line A-A of FIG. 9.

FIG. 9 is an explanatory view showing a total image of the spinal column. FIG. 10 is a sectional view taken along a line A-A of FIG. 9. As shown by FIG. 9, the spinal column 200 shows a state of being circumflexed (twisted) to a minus θ side with regard to areas of J1, J3 and a plus θ side with regard to areas of J2, J4 relative to a center line O, and a line segment 400 shows the state.

FIG. 10 shows a section of an A-A line portion of the vertebra 201 of the vertebrae 200, as a state of circumflexing (twisting) the vertebra 201, there is shown a state of being circumflexed (twisted) to the plus θ side or the minus θ side relative to, for example, the center line O. The state of circumflexing (twisting) the spinal column 200 is measured by the probe 31 of the spinal column measuring apparatus 3, and the measured data of the circumflexed (twisted) angle θ is provided to the image processing apparatus 7

According to the image processing apparatus 7, by providing the inclination β or the circumflex angle between the respective vertebrae provided in this way to the spinal column image data of the basic models the unique state of the spinal column based on the gender and the height of the measurement subject is generated as image data.

Further, the image processing apparatus 7 subjects the image data provided as described above to an image processing by using the three-dimensional computer graphics and transmits a result of the image processing to the display apparatus 9 connected to the image processing apparatus 7. Thereby, a pseudo-spinal column image is displayed on a screen of the display apparatus 9.

FIG. 11 illustrates views showing a spinal column image displayed on the display apparatus by measuring the spinal column by a spinal column measuring apparatus and generating the spinal column by an image processing apparatus based on the measured data in the human spinal column measuring and displaying system according to the invention.

FIG. 11(a) shows an image of the spinal column on the back side generating a total of the measured spinal column and displaying the spinal column from the back side and FIG. 11(b) shows an image of the spinal column on the left side generating the total of the measured spinal column and displaying the spinal column on the left side.

As shown by FIG. 11(a), the total of the spinal column is divided into the cervical vertebrae portion, the upper thoracic vertebrae, the middle thoracic vertebrae, the lower thoracic vertebrae, the lumber vertebrae, the sacral vertebrae, and the coccygeal vertebrae and displayed respectively by being classified by colors according to the embodiment. For example, by displaying to classify by colors such that the cervical vertebrae is "white", the upper thoracic vertebrae is "red", the middle thoracic vertebrae is "blue", the lower thoracic vertebrae is "green", the lumber vertebrae is "yellow" and the sacral vertebrae and the coccygeal vertebrae are "gray", it can easily be recognized optically there is a portion at which the spinal column is bent and in which the direction of the spinal column is bent. Further, since the image for displaying the spinal column is image data of the three-dimensional computer graphics, an image of the spinal column in which the coordinates of the view point are changed by the image data generating means 18 and the image of the spinal column on the left side as shown by FIG. 11(b) can be displayed.

Further, when it is considered that, for example, "bending of the upper thoracic vertebrae is abnormal", only the upper thoracic vertebrae can be displayed.

In a state in which the images of FIG. 11(a) and FIG. 11(b) are displayed, by depressing predetermined keys (for example, "UP key (↑)" or "DOWN key (↓)") provided at the input apparatus 10, the display can be switched to a display of only the upper thoracic vertebrae.

FIG. 12 is a spinal column image generating and displaying the lumber vertebrae, the thoracic vertebrae in the spinal column displayed by FIG. 11, FIG. 12(a) is an explanatory view generating and displaying a side spinal column image of 4 of the thoracic vertebrae (05, 06, 07, 08-th), FIG. 12(b) is an explanatory view generating and displaying a left side spinal column image of 4 of the thoracic vertebrae (09, 10, 11, 12-th), FIG. 12(c) is an explanatory view generating and displaying 5 of the lumber vertebrae (01, 02, 03, 04, 05-th), respectively.

FIG. 12(a) generates and displays a back side spinal column image of the upper thoracic vertebrae, and front and rear bent angles, left and right inclinations and circumflex angles are displayed with regard to the fifth thoracic vertebra, the sixth thoracic vertebra, the seventh thoracic vertebra, the eighth thoracic vertebra referred to as the upper vertebrae in the thoracic vertebrae.

Further, along with the image of the upper thoracic vertebrae when the angles in the front and rear direction and bent angles in the left and right direction are calculated for example, an explanation of the bent angles in the front and rear direction may be displayed such that for example, with regard to the bent angles in the front and rear directions, the bent angle of the sixth thoracic vertebra relative to the fifth thoracic vertebra is "angle of fifth thoracic vertebra→angle of sixth thoracic vertebra=rear bent 0.1 [degree]", . . . , the bent angle of the ninth thoracic vertebra relative to the eighth thoracic vertebra is "front bent of eighth thoracic vertebra→ninth thoracic vertebra=front bent 0.0 [degree]". Similarly, the bent state of the spinal column may be displayed by displaying the explanation of angles of inclination in left and right direction such that with regard to bent angle in left and right direction, left and right inclination of the sixth thoracic vertebra relative to the fifth thoracic vertebra is "fifth thoracic vertebra→sixth thoracic vertebra=right up 0.1 [degree]", . . . , bent angle of the ninth thoracic vertebra relative to the eighth thoracic vertebra is "left and right inclination of eighth thoracic vertebra→ninth thoracic vertebra=right down 0.1 [degree]" or the like.

In addition thereto, along with the image of the upper thoracic vertebrae, a circumflex (twist) state is calculated, an explanation of a circumflex (twist) angle may be displayed such that, for example, with regard to a circumflex (twist) angle in front and rear direction, a circumflex (twist) angle of the sixth thoracic vertebra relative to the fifth thoracic vertebra is "circumflex (twist) angle of fifth thoracic vertebra→sixth thoracic vertebra=right front 7.0 [degree]", . . . , a circumflex (twist) angle of the ninth thoracic vertebra relative to the eighth thoracic vertebra is "circumflex (twist) of eighth thoracic vertebra→ninth thoracic vertebra=right front 2.4 [degree]". Similarly, the bent state of the spinal column may be displayed with regard to a bent angle in left and right direction such that left and right inclination of the sixth thoracic vertebra relative to the fifth thoracic vertebra is "fifth thoracic vertebra→sixth thoracic vertebra=right up 0.1 [degree]", . . . , a bent angle of ninth thoracic vertebra relative to eighth thoracic vertebra is "left and right inclination of eighth thoracic vertebra→ninth thoracic vertebra=right down 0.1 [degree]" or the like.

Further, in a state of displaying the back side spinal column image of the upper thoracic vertebrae as shown by FIG. 12(a), by depressing the predetermined key (for example, "UP key (↑)" or "DOWN key (↓)" provided at the input apparatus 10, a view point can be changed, and an image moving the currently displayed upper thoracic vertebrae to a lower side can be displayed.

For example, in the state of displaying the back side spinal column image of the upper thoracic vertebrae of FIG. 12(a), when "DOWN key (↓)" is depressed as shown by FIG. 12(b), the thoracic vertebrae image on the lower side of the upper thoracic vertebrae is displayed, similar to the above-described, the front and rear bent in the front and rear direction, the left and right inclination and the circumflex (twist) angle are calculated and displayed respectively.

Next, in the state of displaying the left side face spinal column image of the upper thoracic vertebrae as shown by FIG. 12(b), by depressing "DOWN key (↓)" provided at the input apparatus 10, as shown by FIG. 12(c), the spinal column image of the lumber vertebrae is displayed, similar to the above-described, front and rear bent in front and rear direction, left and right inclination and circumflex (twist) angle are respectively displayed.

That is, according to the image processing apparatus 7 according to the invention, the spinal column image is formed based on the basic diagram database 74d and the vertebrae table 74e, a specific value by the measured data is reflected thereto, the vertebra at the portion is moved in coordinates thereof in a predetermined direction to be displayed, thereby, a total of the spinal column as shown by FIG. 11 or a portion thereof as shown by FIG. 12 is displayed from the back side, by depressing the predetermined key, the state of moving the position of the spinal column is simulated and displayed. In this way, it can easily be recognized optically how which vertebra is bent in a plurality of vertebrae constituting the spinal column.

Next, an explanation will be given of a behavior of measuring a state of the spinal column of the human body to be displayed three-dimensionally by a computer graphics by the human spinal column measuring and displaying system 1 according to the invention in reference to flowcharts of FIG. 13 through FIG. 15.

Figure 13:
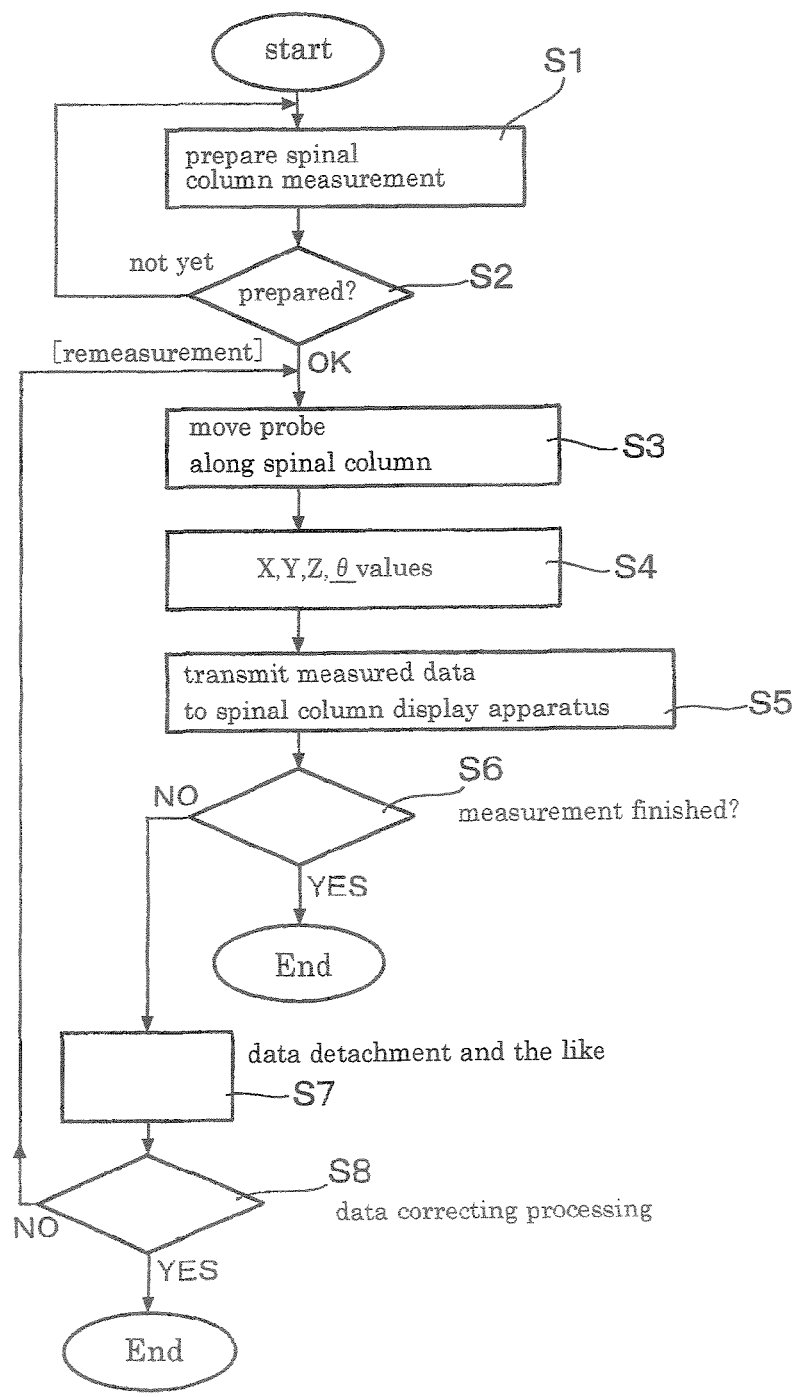
FIG. 13 is a flowchart for explaining a flow of a total of measurement for measuring a state of the spinal column of a patient (measurement subject).

FIG. 13 is a flowchart for explaining a total flow of measurement for measuring a state of the spinal column of a patient (measurement subject).

In order to measure a state of the spinal column of the patient (measurement subject), a power source of the human spinal column measuring and displaying system 1 is inputted, the patient (measurement subject) is made to lie down on the measuring bed 32 to prepare for measurement (step S1).

According thereto, when the power source is inputted, preparation is finished when a value displayed on the coordinate detecting system 38, for example, X value and Y value become "0" or "1".

Further, it is checked whether the preparation is finished (step S2), when the preparation is not finished the operation returns to the processing of step S1 to carry out the preparation. When the preparation is finished the measuring person holds the probe 31 by the hand to move to a direction of the head portion of the patient (measurement subject) to arrange on the spinal column on the side of the cervical vertebrae to move along the spinal column to the side of the luster vertebrae (step S3).

When the probe 31 is moved, recesses and projections and a degree of bending of the spinal column are detected as X value, X value, Z value θ value (step S4). The detected measured data is transmitted to the image processing apparatus 7 (step S5). Further, it is determined whether measurement is finished (step S6), when measurement is finished, the processings are finished. When measurement is not finished yet (step S6; NO), a data detaching processing or other processing is executed (step S7), when data correcting processing is not finished step S8; NO), the operation returns to the processing of step S3 to successively move the probe 31 on the spinal column.

Figure 14:
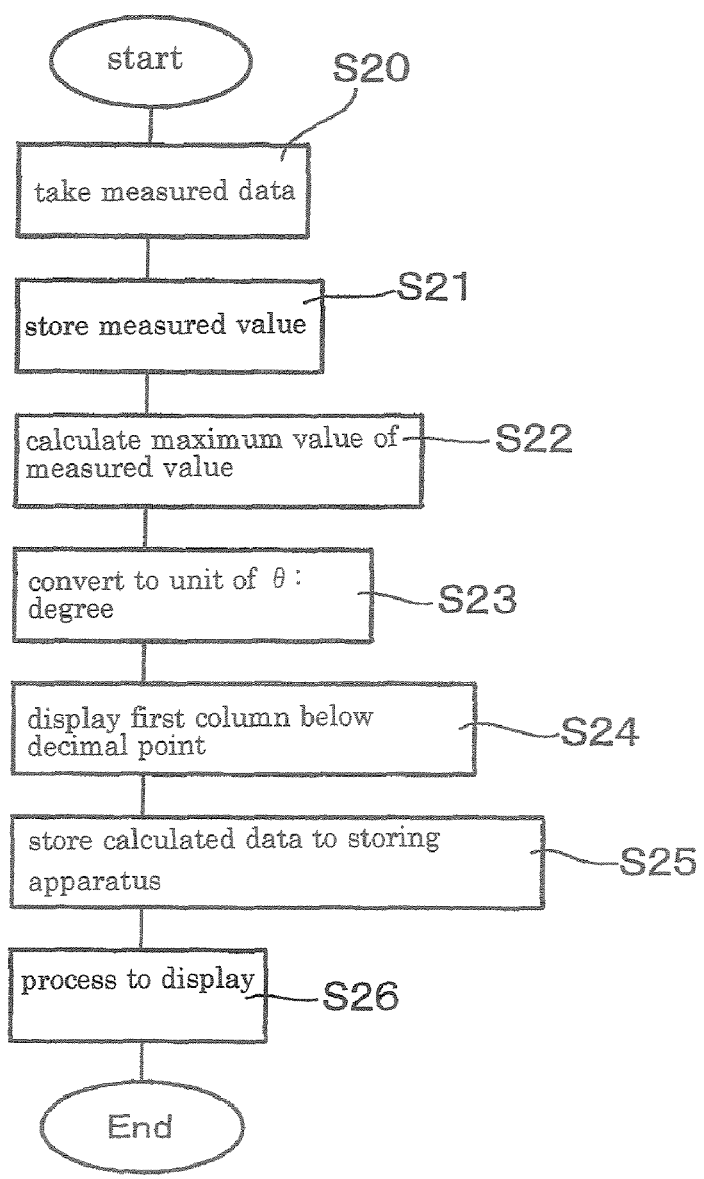
FIG. 14 is a flowchart of a circumflex angle measuring processing of a measured data by the image processing apparatus of the human spinal column measuring and displaying system according to the invention.

FIG. 14 is a flowchart of a circumflex angle measuring processing of a measured data by the image processing apparatus of the human spinal column measuring and displaying system according to the invention.

Next, when the measured data is received by the image processing apparatus 7 (step S20), the measured data is stored to the measured data storing means 74c by CPU 71 (step S21), maximum values are calculated from data of X values, Y values, Z values of the measured data of 1 mm or smaller by the converting means 71a, a maximum value of an absolute value of the circumflex angle θ is calculated (step S22). The first lower column of the maximum value becomes equal to or smaller than the decimal point, and therefore, the maximum value is converted to a millimeter unit by attaching the decimal point. Here, the value equal to or smaller than the decimal point is conceived as the error in measurement, and therefore, the number equal to or smaller than the decimal point of the measured data is rounded down to constitute an integer.

Furthers the converting means 71a realized by CPU 71 of the image processing apparatus 7 converts data of circumflex (twist) angle θ to a degree unit (step S23). Further, the converting means 71a displays the first lower column of the decimal point of the measured data such that, for example 5.5 [degrees] (step S24). The measured data converted into predetermined integer or angle by the converting means 71a in this way is stored to the converted data storing means 71c by the converting means 71a (step S25). Further, after carrying out the image processing by the synthesizing means 71c and the image data generating means 71d, the image data is displayed (step S26).

Figure 15:
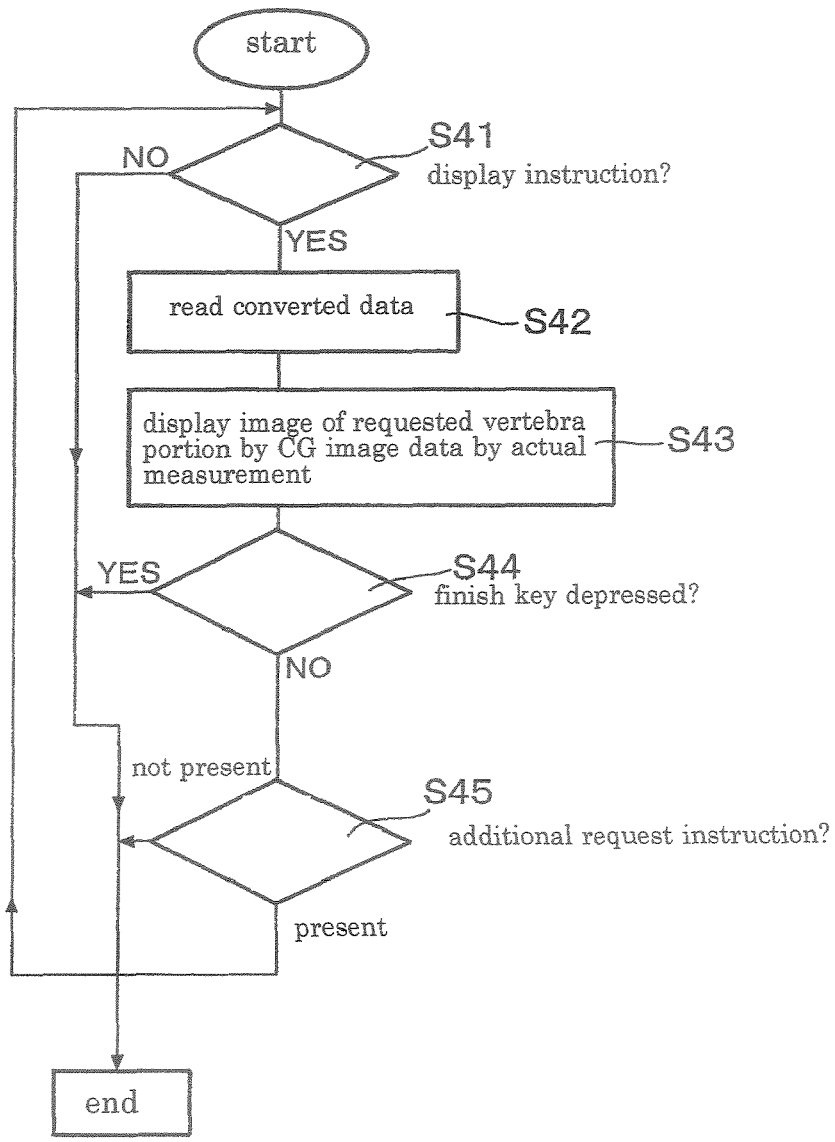
FIG. 15 is a flowchart of a processing of displaying a state of bending the spinal column generated based on a measured data by a computer graphics according to the human spinal column measuring and displaying system according to the invention.

FIG. 15 is a flowchart for processing to display a state of bending the spinal column generated based on the measured data by a computer graphics in the human spinal column measuring and displaying system according to the invention.

In order to display a state of the spinal column by using a computer graphics a predetermined instruction is inputted from the input apparatus 5 of a mouse or the like connected to the image processing apparatus 7 (step S41), when an instruction is not executed (step S41; NO), the processing is finished.

When a display instruction is carried out from the input apparatus 5 to the image processing apparatus 7 (step S41; YES), a converted data (data subjected to a predetermined conversion based on the measured data) is read from the converted data storing means 73a (step S42), an image data of a basic model of the spinal column based on gender, height of the measurement subject is formed in reference to the basic diagram database and the vertebrae table 74e based on an image processing software program (human spinal column measuring and displaying program) executed by the image processing apparatus 7, further, a three-dimensional vertebrae image data of the measurement subject is generated by reflecting the converted data (data subjected to predetermined conversion based on measured data) to the three-dimensional vertebrae image data of the basic model, and the data is transmitted to the display apparatus 9 (step S43).

Thereby, a three-dimensional pseudonymous vertebrae image is displayed on a display screen of the display apparatus 9. Here, the image processing apparatus 7 determines whether a finish key is depressed (step S44), when the finish key is depressed (step S44; YES), the processing is finished.

Further, the image processing apparatus 7 determines whether the finish key is depressed (step S44), when it is determined that the finish key is not depressed (step S44; NO), the image processing apparatus 7 proceeds to determine whether an additional display is requested (step S44). The determination items are "display of total", "display of only cervical vertebra", "display of only thoracic vertebra", "display of only lumber vertebra", "display of only sacral vertebra", "display of only coccygeal vertebra" and the like. The image processing apparatus 7 determines the determination item (step S45), when there is the determination item (step S45; present), the image processing apparatus 7 carries out a processing for executing the display instruction in accordance with the display item and thereafter returns to step S42.

Further, the image processing apparatus 7 finishes the processing when the additional display is not requested (step S45; not present).

According to the image of the spinal column generated in this way, bendings to the left and to the right displayed from the back face are optically recognized, further, the spinal column image is displayed from left and right side faces to be able to optically recognize bendings to the front and to the rear, when an arrow mark key (→ or ←) is depressed the display is carried out by moving the view point in the predetermined direction by 90 degrees, when an up key is depressed, it is determined whether the topmost portion (upper thoracic vertebra portion) is displayed, when the topmost portion is displayed, the currently display portion is displayed as it is since the further upper portion cannot be displayed, and when the portion is not a topmost portion, a processing of displaying an upper portion of the currently displayed portion is executed by the image processing apparatus 7.

Further, when a down key is depressed it is determined whether the bottommost portion (sacrococcygeal vertebra portion) is displayed, when the bottommost portion is displayed, the currently displayed portion is displayed as it is since further lower portion cannot be displayed, when the portion is not the bottommost portion, a processing of displaying a lower portion of the currently displayed portion is executed by the image processing apparatus 7.

That is, in order to measure and display the state of bending the spinal column by utilizing the human spinal column measuring and displaying system 1 of the invention, the gender and the height of the patient (measurement subject) are needed, further, a state before treatment (symptom of neck, shoulder, back, waist or the like) is provided by a questioning diagnosis or description of a preliminary diagnosis paper.

Further, the state of the spinal column is measured as described above, and is displayed on a display screen of the display apparatus 9 by a three-dimensional computer graphics.

An explanation is given to the patient (measurement subject) while showing a displayed image of the spinal column, and a treatment is carried out for a portion of the spinal column bent in comparison with that in a normal state.

When the treatment is finished, the state of the spinal column is measured again, and pseudonymous spinal column is displayed on the display screen of the display apparatus 9 by the three-dimensional computer graphics.

Further, by providing the image data of the state of the spinal column before treatment and after treatment from the image processing apparatus 7 to the display apparatus 9, the images displayed on the display screen of the display apparatus 9 or images outputted to print can be seen and compared.

By displaying the states of bending the spinal column before treatment and after treatment by the spinal column image in this way, both of the operator and the patient (measurement subject) can be informed of the state of bending the spinal column easily.

As explained above, according to the human spinal column measuring and displaying system of the invention, in what state the spinal column is bent can optically be recognized by the pseudonymously formed three-dimensional image by a simple method of scanning the probe on the spinal column of the lying down measurement subject from the surface.

Thereby, there is achieved an advantage that the operator can easily execute the treatment by explaining by what degree the spinal column is bent before treatment and after treatment by the image.

Further, the patient who is the measurement subject can optically recognize the state of the spinal column similar to actual as the image nor by specialized medical terms, and therefore, the patient can easily understand how and to which what portion of the spinal column of the patient per se is bent.

Further, although according to the embodiment, the probe is explained as an inverse T-like type, the shape is not particularly limited so far as the probe can scan on the spinal column.

Further, although according to the embodiment, an explanation has been given such that the image of the vertebrae is generated by reading corresponding data from the basic diagram data and the vertebrae table, the vertebrae image in correspondence with the height and the gender of the measurement subject may be provided as a database, and a style of data for visualizing the vertebrae or a storing method are not particularly limited so far as the vertebrae of the respective measurement subject can be displayed.

Further although in the embodiment, the explanation has been given by displaying the vertebrae image by the three-dimensional computer graphics and moving the view point by 90 degrees, the view point may be moved by 45 degrees, and the range of moving the view point is not particularly limited.

Figure 16:
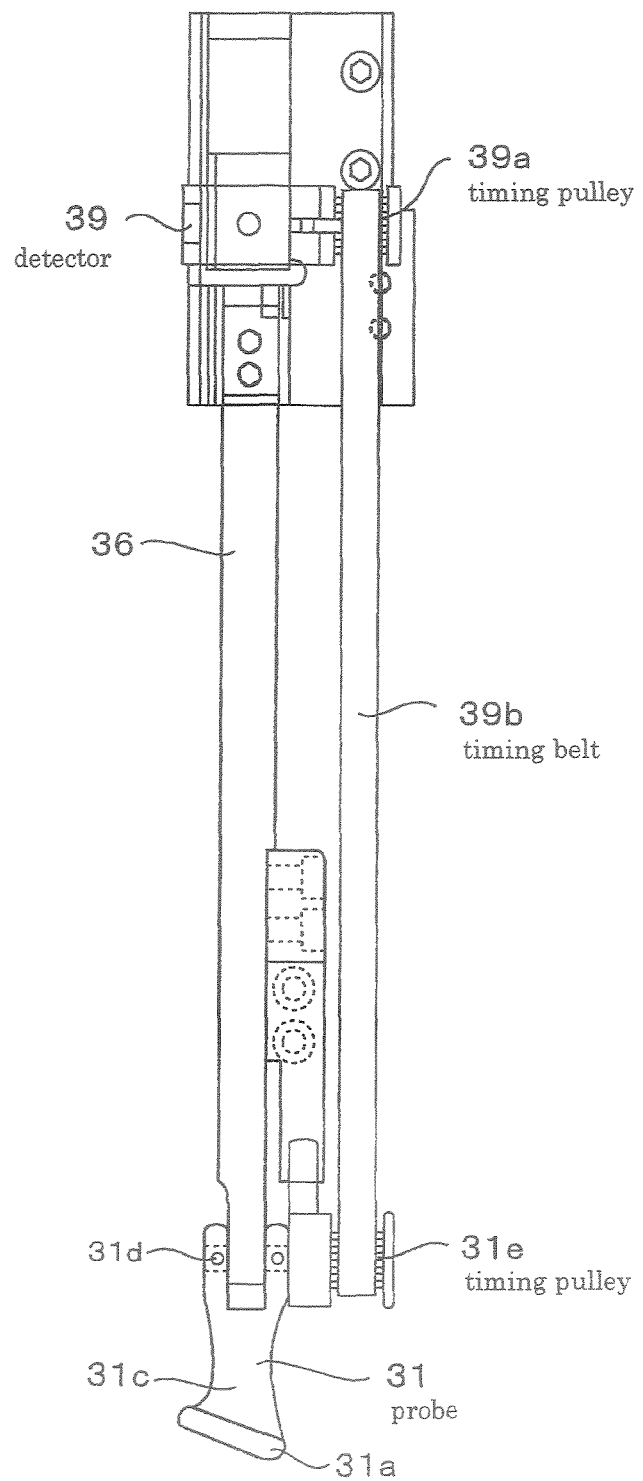
FIG. 16 is a view showing other constitution example of a mechanism for measuring a circumflex (twist) angle θ by the probe of the spinal column measuring apparatus of the human spinal column measuring and displaying system according to the invention.

FIG. 16 is a view showing other constitution example of a mechanism of measuring a circumflex (twist) angle θ by a probe of the spinal column measuring apparatus of the human spinal column measuring and displaying system according to the invention.

According to the mechanism of measuring the circumflex (twist) angle θ shown in FIG. 16, a fixed piece 31c of the probe 31 is fixed to a distal end of a vertical support arm 36 pivotably by a pivoting shaft 31d, there is provided a structure when an angle detector cannot be attached to a vicinity of the pivoting shaft 31d.

That is, according to the other measuring mechanism of the circumflex (twist) angle θ according to the embodiment of the invention, a timing pulley 31e is fixed to the pivoting shaft 31d of the probe 31, and rotation of the pivoting shaft 31d is made to be able to be transmitted to the timing pulley 31e. Further, according to other measuring mechanism of the circumflex (twist) angle θ according to the embodiment of the invention, an angle detector 39 is fixed to an upper portion of the vertical support arm 36, a timing pulley 39a is fixed to a pivoting shaft of the angle detector 39, and an amount of pivoting the timing pulley 39a is made to be able to be transmitted to the angle detector 39. Further, according to other measuring mechanism of the circumflex (twist) angle θ according to the embodiment of the invention, a timing belt 39b is hung between the timing pulley 31e and the timing pulley 39a, and an amount of pivoting the fixed piece 31c of grasping pieces 31a, 31b of the probe 31 is made to be able to be transmitted to the angle detector 39 by way of the timing pulley 31e and the timing belt 39b and the timing pulley 39a.

By adopting such a structure, even when the angle detector cannot be attached around the probe 31, the circumflex (twist) angle is made to be able to be measured by the probe 31. Further, although the embodiment of the invention has been explained as the measuring apparatus of lying down type, the embodiment is applicable also to a measuring apparatus of an erected type or a seated type or the like.

Figure 17:
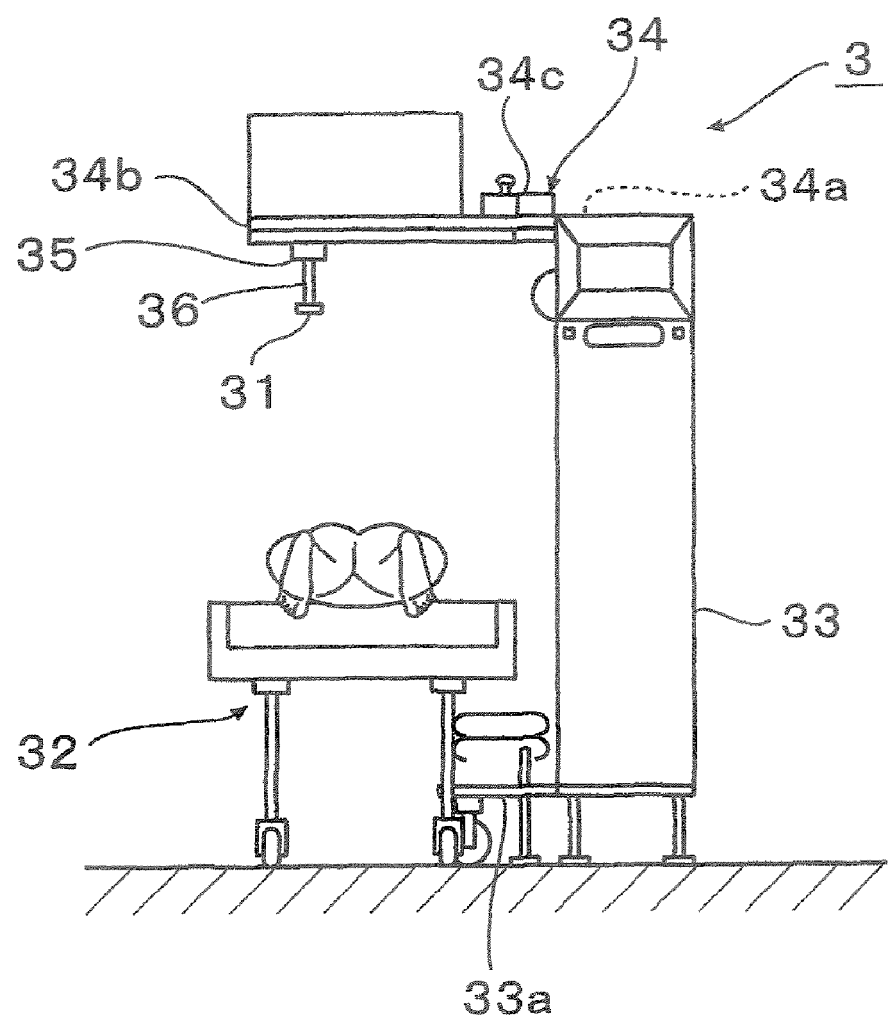
FIG. 17 is a side view of a mechanism portion of the spinal column measuring apparatus shown in FIG. 1 in the human spinal column measuring and displaying system according to the invention.
Figure 18:
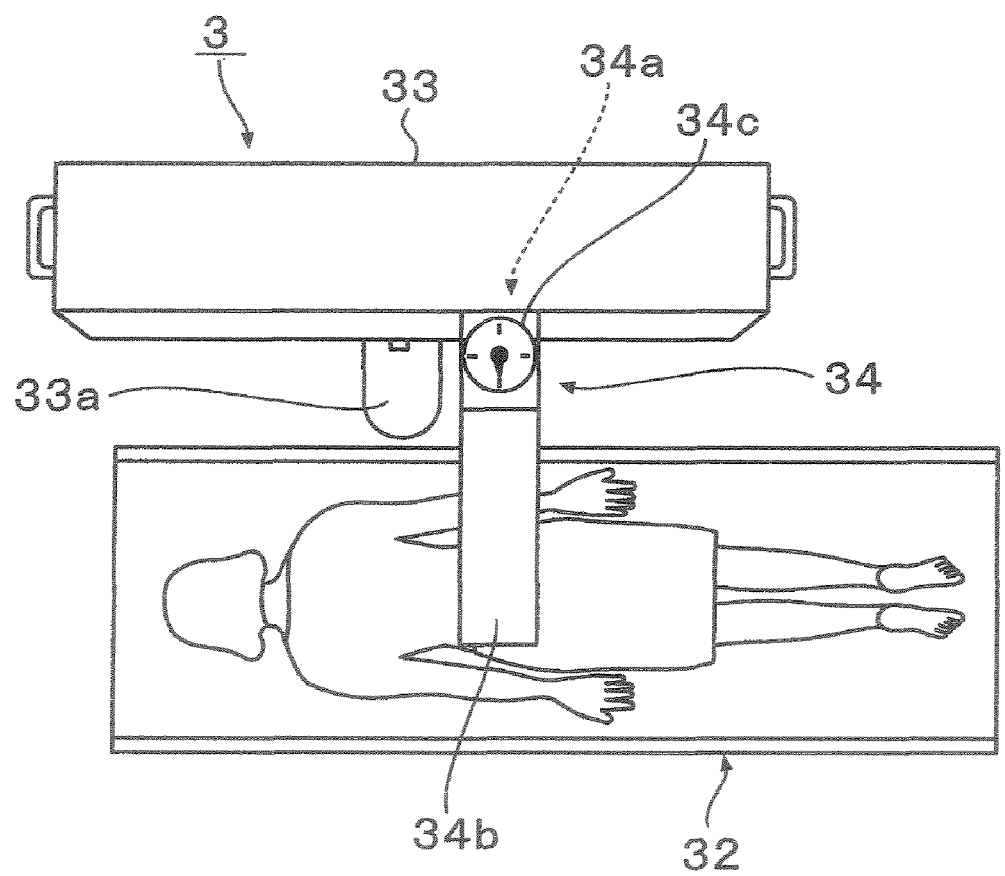
FIG. 18 is a plane view of the mechanism portion of the spinal column measuring apparatus shown in FIG. 1 in the human spinal column measuring and displaying system according to the invention.

FIG. 17 is a side view of the mechanism portion of the spinal column measuring apparatus shown in FIG. 1 in the human spinal column measuring and displaying system according to the embodiment. FIG. 18 is a plane view of the mechanism portion of the spinal column measuring apparatus shown in FIG. 1.

In FIG. 17 and FIG. 18, although the spinal column measuring apparatus 3 has already been explained, when explained again, the spinal column measuring apparatus 3 includes the mechanism portion comprising the measurement bed 32 on which the measuring subject lies in the lying down state, the base 33 fixed to a side of the one side face of the measurement bed 32 and provided vertically, the measuring direction support arm 34 movably fixed to the base 33 in left and right direction (X direction) of the drawing, the parallel support arm 35 fixed to the measuring direction support arm 34 and made to be movable in the vertical direction (Y axis direction) of the drawing, the vertical support arm 36 fixed to the parallel support arm 35 and made to be movable in up and down direction (Z axis direction) of the drawing, and the probe 31 pivotably fixed to the front end of the vertical support arm 36. Further, as shown by FIG. 17 and FIG. 18, a lower portion of the base 33 is provided with a tumble down preventing member 33a to extend in a direction the same as that of the measuring direction support arm 34.

The measuring direction support arm 34 includes a moving mechanism 34a comprising a rail fixed to the base 33 and a slider movably fixed to the rail, an attaching seat 34b attaching to fix the parallel support arm 35, and a pivoting mechanism 34c interposed between the slider of the moving mechanism 34a and the attaching seat 34b for making the attaching seat 34b pivotable in a vertical face. Further, the pivoting mechanism 34c may be constituted by a mechanism interposed between the slider of the moving mechanism 34a and the attaching seat 34b for making the attaching seat 34b pivotable in a vertical face.

Further, the pivoting mechanism 34c also includes an automatic lock mechanism by which when the attaching seat 34b is disposed at a position of capable of carrying out measurement, the attaching seat 34b is fixed at the position, and a releasing mechanism for releasing the automatic lock mechanism when the attaching seat 34b is pivoted.

Figure 19:
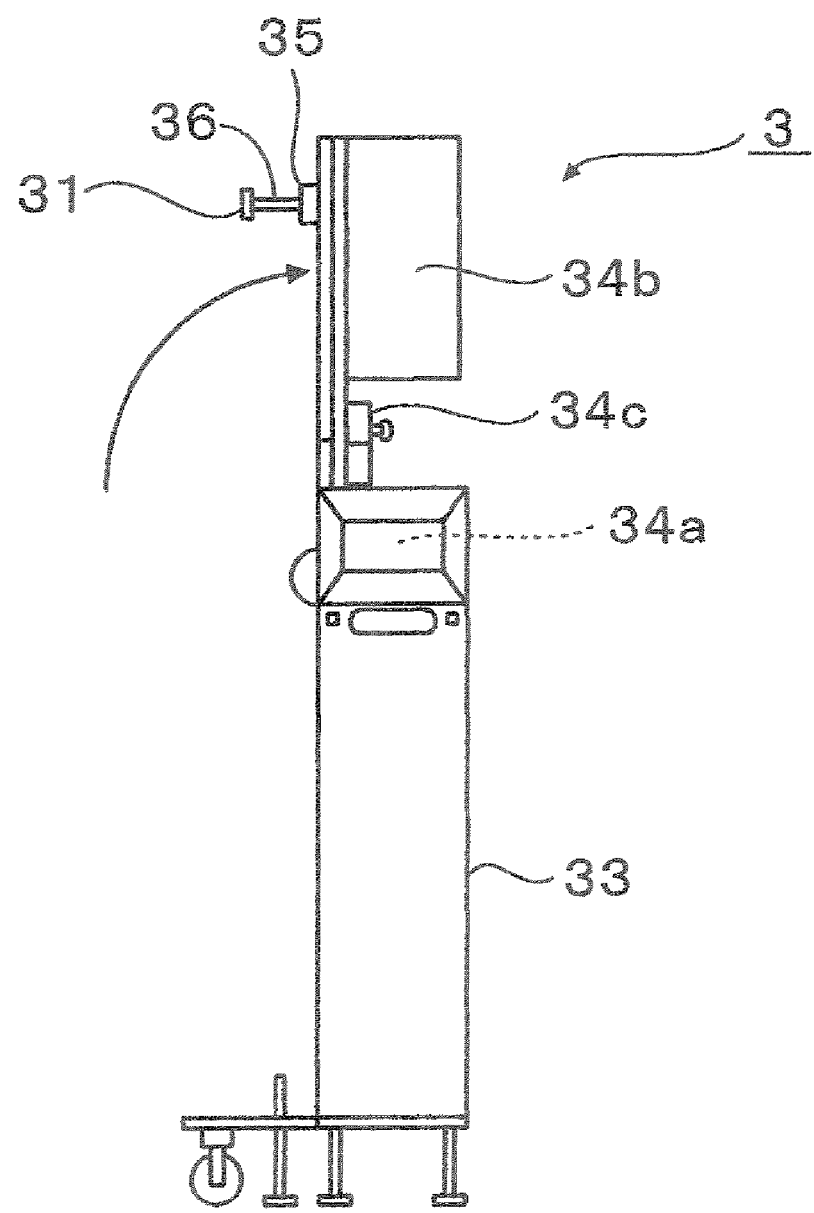
FIG. 19 is a plane view of the mechanism portion of the measuring director support arm in a vertical face in the human spinal column measuring and displaying system according to the invention.
Figure 20:
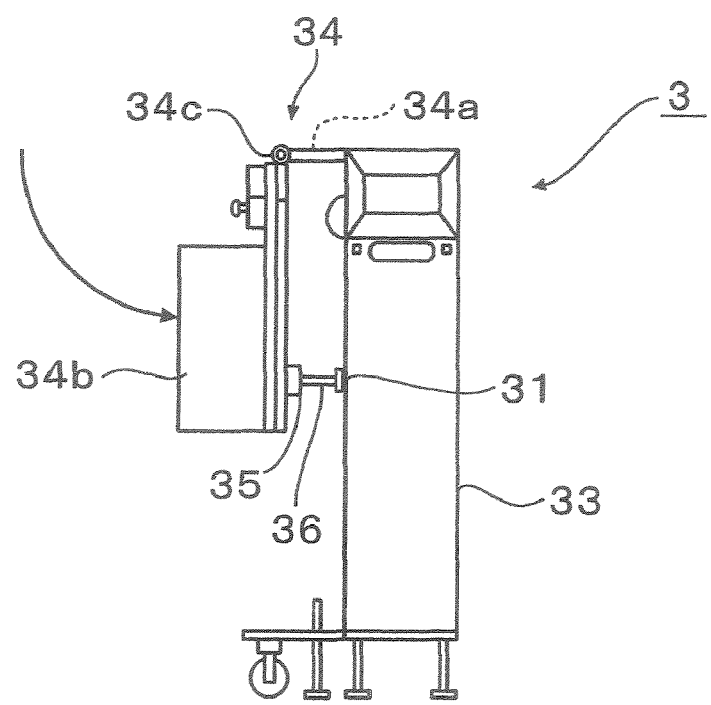
FIG. 20 is a view showing an embodiment of rotating the measuring direction support arm in the vertical face in the human spinal column measuring and displaying system according to the invention.

FIG. 19 and FIG. 20 are views showing an embodiment of pivoting the measuring direction support arm in the vertical face in the human spinal column measuring and displaying system according to the invention.

The measuring direction support arm 34 shown in FIG. 19 is an example of constituting the attaching seat 34b to print in an upper direction. Thereby, the attaching seat 34b or the like does not constitute a hindrance and the subject is simplified to lie down on the bed.

The measuring direction support arm 34 shown in FIG. 20 is an example of constituting the attaching seat 34b to pivot in a lower direction. Thereby, the attaching seat 34b or the like does not constitute a hindrance and the subject is simplified to lye down on the bed.

FIG. 21 through FIG. 24 are views showing an embodiment of pivoting the measuring direction support arm in a horizontal face in the human spinal column measuring and displaying system according to the invention.

Figure 21:
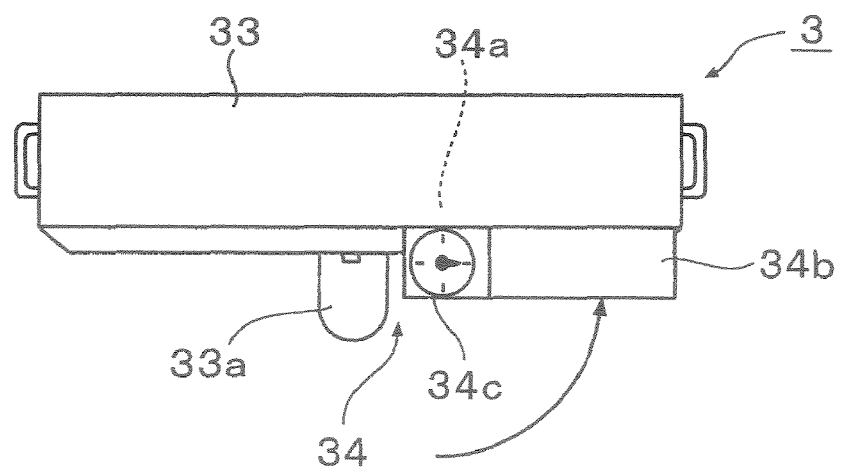
FIG. 21 is a view showing an embodiment of rotating the measuring direction support arm in a horizontal face in the human spinal column measuring and displaying system according to the invention.

The measuring direction support arm 34 shown in FIG. 21 is an example of constituting the attaching seat 34b to pivot by an angle of 90 [degrees] in a right direction in a horizontal face. Thereby, the attaching seat 34b or the like does not constitute a hindrance and the subject is simplified to lie down on the bed.

Figure 22:
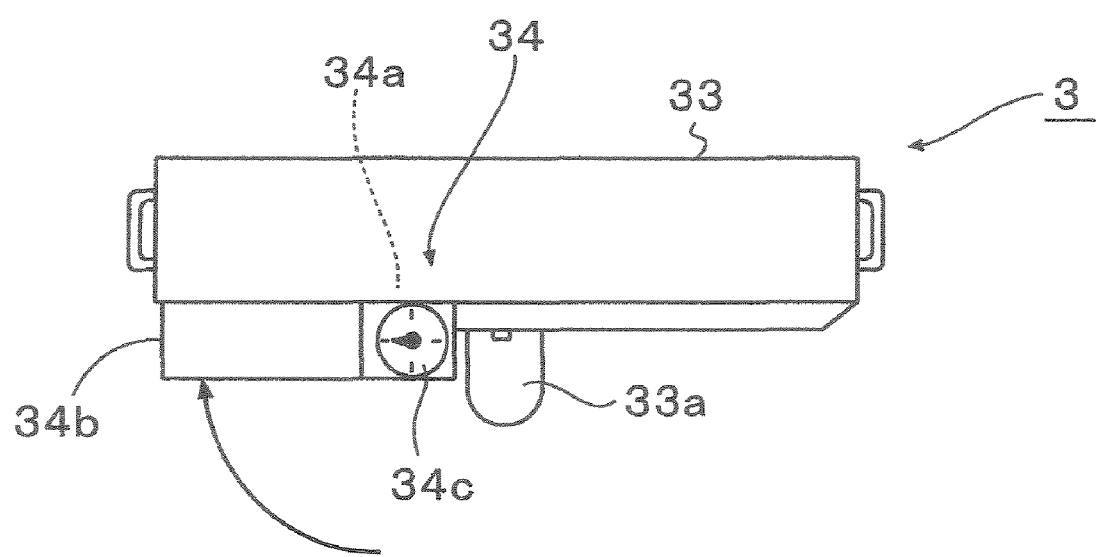
FIG. 22 is a view showing an embodiment of rotating the measuring direction support arm in the horizontal face in the human spinal column measuring and displaying system according to the invention.

The measuring direction support arm 34 shown in FIG. 22 is an example of constituting the attaching seat 34b by an angle of 90 [degrees] in a left direction in a horizontal face. Thereby, the attaching seat 34b or the like does not constitute a hindrance and the subject is simplified to lie down on the bed.

Figure 23:
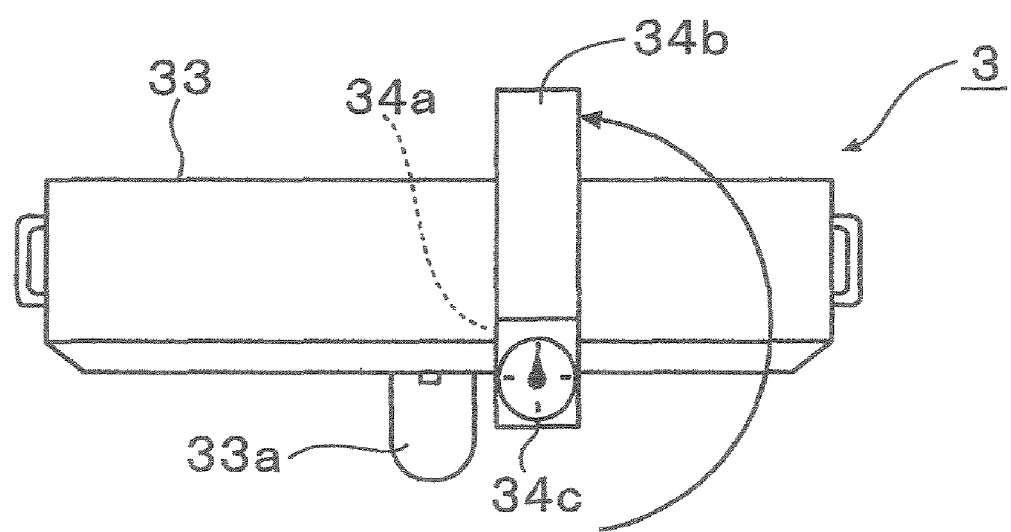
FIG. 23 is a view showing an embodiment of rotating the measuring direction support arm in the horizontal face in the human spinal column measuring and displaying system according to the invention.

The measuring direction support arm 34 shown in FIG. 23 is an example of constituting the attaching seat 34b by an angle of 180 [degrees] in a right direction in a horizontal face. Thereby, the attaching seat 34b or the like does not constitute a hindrance and the subject is simplified to lie down on the bed.

Figure 24:
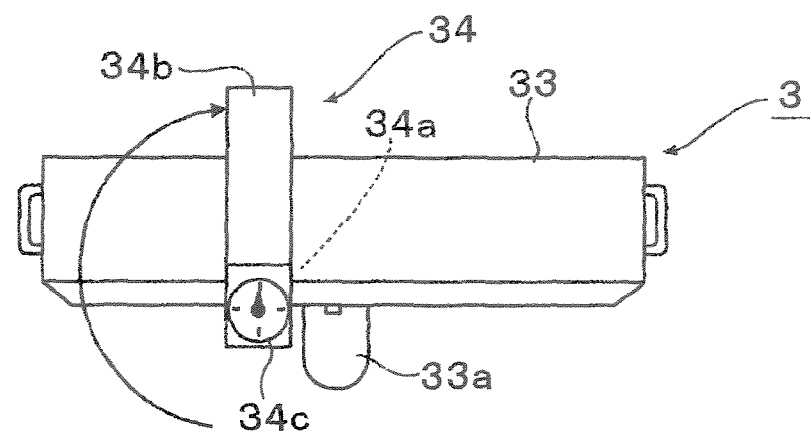
FIG. 24 is a view showing an embodiment of rotating the measuring direction support arm in the horizontal face in the human spinal column measuring and displaying system according to the invention.

The measuring direction support arm 34 shown in FIG. 24 is an example of constituting the attaching seat 34b by an angle of 180 [degrees] in a left direction in a horizontal face. Thereby, the attaching seat 34b or the like does not constitute a hindrance and the subject is simplified to lie down on the bed.

Figure 25:
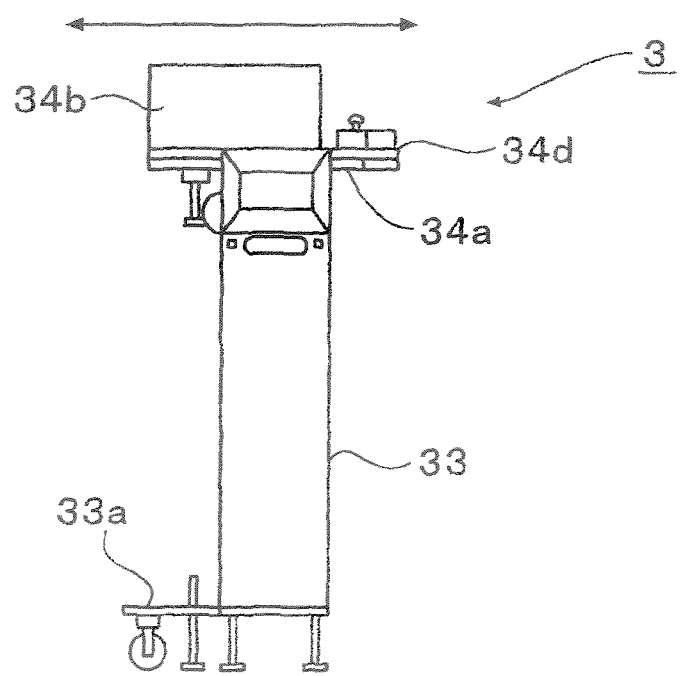
FIG. 25 is a view showing an embodiment of sliding the measuring direction support arm in the horizontal face in the human spinal column measuring and displaying system according to the invention.

FIG. 25 is a view showing an embodiment of sliding the measuring direction support arm in a horizontal face in the human spinal column measuring and displaying system according to the invention.

In FIG. 25, the measuring direction support arm 34 at least includes a moving mechanism 34a comprising a rail fixed to the base 33 and a slider movably fixed onto the rails the attaching seat 34b attaching to fix the parallel support arm 35, and a horizontal slide mechanism 34d interposed between the slider of the moving mechanism 34a and the attaching seat 34b for making the attaching seat 34b movable in a horizontal direction.

By moving the attaching seat 34b as shown by FIG. 25 by the horizontal slide mechanism 34d, the attaching seat 34b or the like does not constitute a hindrance and the subject is simplified to lie down on the bed.

Figure 26:
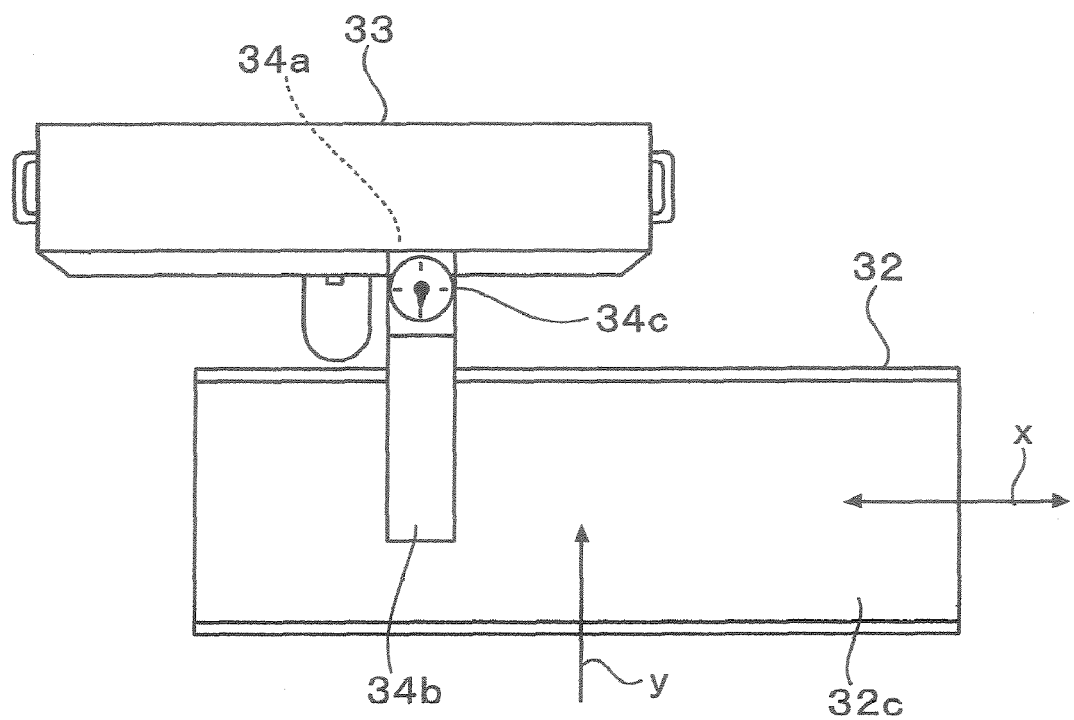
FIG. 26 is a plane view showing an example of moving the bed in the human spinal column measuring and displaying system according to the invention.
Figure 27:
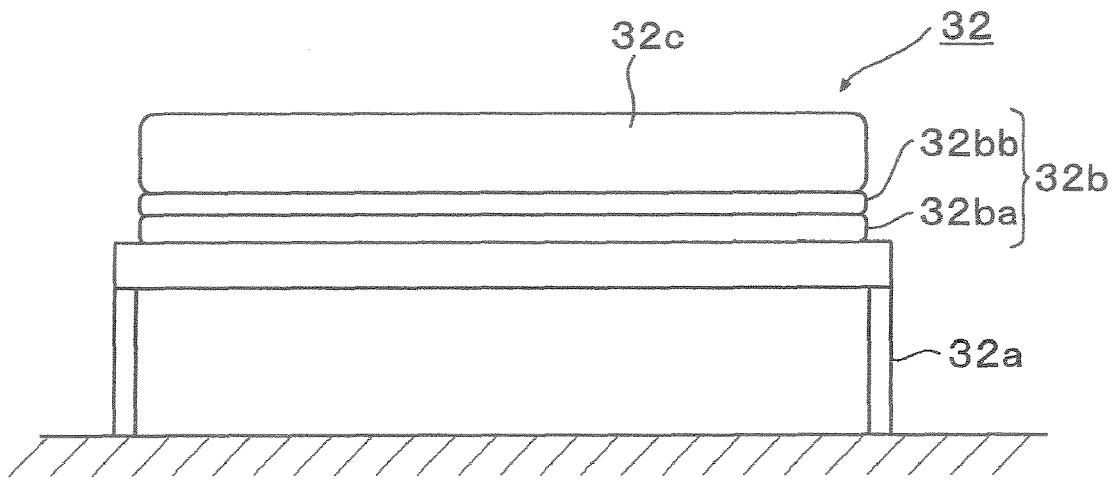
FIG. 27 is a constitution view showing an embodiment of sliding in a bed face in the human spinal column measuring and displaying system according to the invention.

FIG. 26 is a plane view showing an example of moving the bed in the spinal column measuring and displaying system according to the invention. FIG. 27 is a constitution view showing an embodiment of sliding in a bed face in the human spinal column measuring and displaying system according to the invention.

The measurement bed 32 is constituted by a base portion 32a installed on a floor, a movable mechanism 32b comprising a fixed bed 32ba fixed onto the base portion 32a and a moving base 32bb horizontally movable on the fixed base 32ba, and a bed sheet portion 32c fixed onto the moving bed 32bb of the movable mechanism 32b.

The constitution is constructed in this way, and therefore, the measurement bed 32 is moved as shown by arrow marks x, y of FIG. 26, and therefore, the bed sheet portion 32c can be moved at a location of being remote from the attaching seat 34b or the like, the attaching seat 34b or the like does not constitute a hindrance and the subject is simplified to lie down on the bed.

Figure 28:
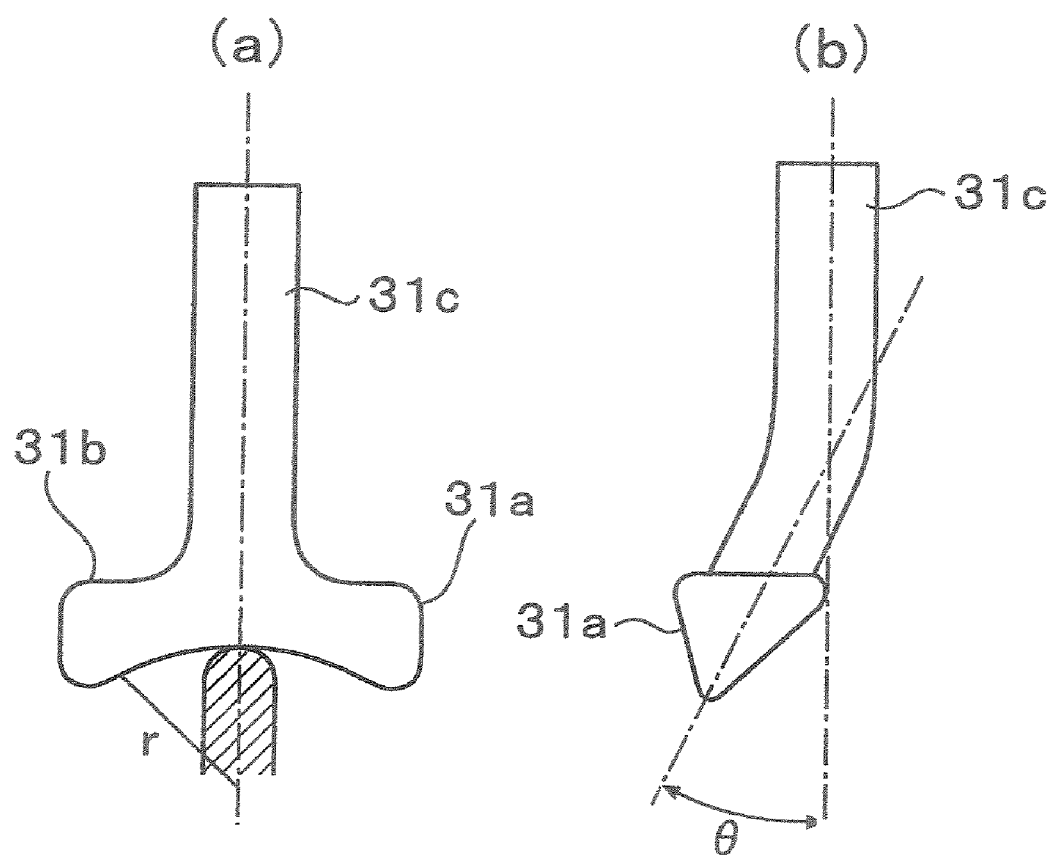
FIG. 28 illustrates an embodiment of a probe in the human spinal column measuring and displaying system according to the invention, FIG. 28($a$) is a front view, FIG. 28($b$) is a side view.

FIG. 28 illustrates views showing an embodiment of a probe in the human spinal column measuring and displaying system according to the invention, FIG. 28(a) is a front view, FIG. 28(b) is a side view.

In FIG. 28(a), and FIG. 28(b), the probe 31 is formed substantially in a T-like shape by the grasping pieces 31a, 31b which are formed by predetermined lengths and on which the second finger and the third finger of the measuring person touch, and the fixed piece 31c formed by the predetermined length at a center position of the grasping pieces 31a, 31b, and the distal end of the fixed piece 31c is pivotably fixed to a lower end of the vertical support arm (refer to FIG. 2; notation 36) by way of the rotating shaft (refer to FIG. 2; notation 31d).

The grasping pieces 31a, 31b are formed in a recess shape by a predetermined arc (circular arc of radius r) on sides thereof brought into contact with the spiral column. Further, as shown by FIG. 28(b), the grasping piece 31a is formed in a triangular shape in a section thereof. The grasping piece 31b is also similarly formed, although not illustrated.

Further, as shown by FIG. 28(b), the fixed piece 31c is formed to bend by a predetermined angle (angle θ) at vicinities of the grasping pieces 31a, 31b in a face orthogonal to a horizontal face including the grasping pieces 31a, 31b and in a direction orthogonal to an axial direction of the grasping pieces 31a, 31b.

By constituting such a shape, a way of use of the probe 31 is improved for the measuring person.

Figure 29:
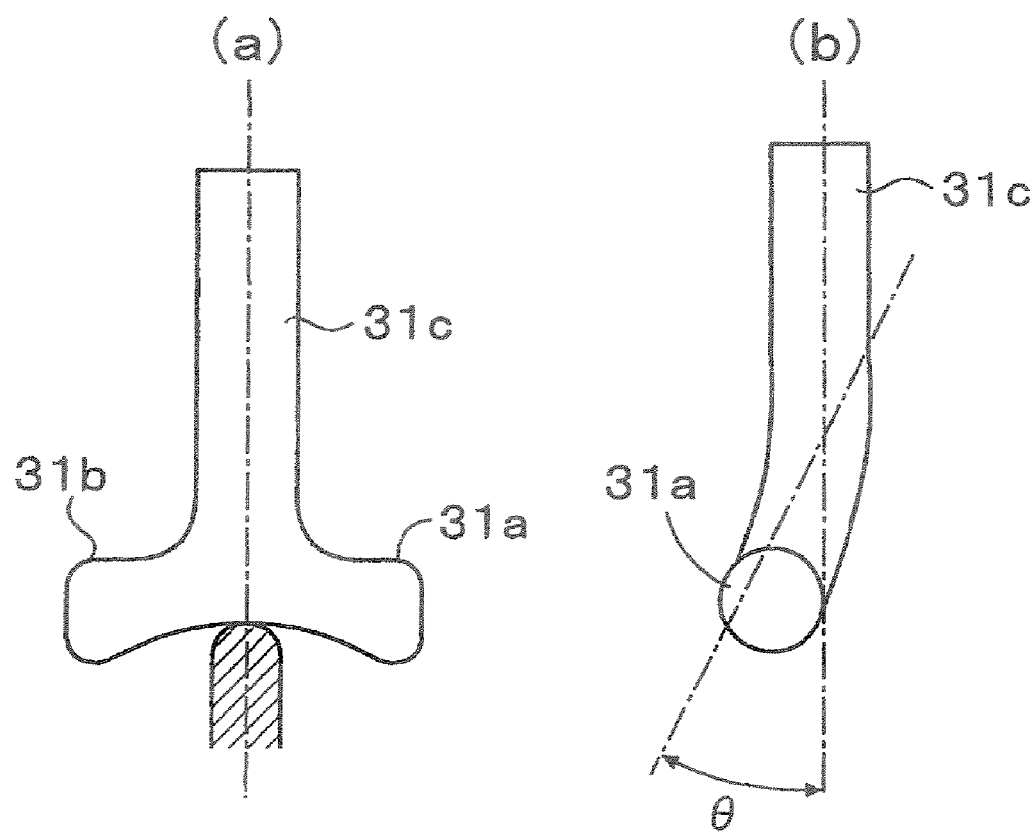
FIG. 29 illustrates views showing an embodiment of a probe in the human spinal column measuring and displaying system according to the invention, FIG. 29($a$) is a front view, FIG. 29($b$) is a side view.

FIG. 29 illustrates views showing an embodiment of a probe in the human spinal column measuring and displaying system according to the invention, FIG. 29(a) is a front view, FIG. 29(b) is a side view.

In FIG. 29(a) and FIG. 29(b), the probe 31 is the same as that in the embodiment shown in FIG. 28 in that the probe 31 is formed substantially by the T-like shape by the grasping pieces 31a, 13b, the fixed piece 31c.

Further, the grasping pieces 31a, 31b are formed in a recess shape by a predetermined arc (circular arc of radius r) on sides thereof brought into contact with the spinal column. Further, as shown by FIG. 29(b), the grasping piece 31a is formed in a circular shape in a section thereof. Also the grasping piece 31b is formed by a similar section, although not illustrated.

Further, as shown by FIG. 29(b), the fixed piece 31c the same as that of the embodiment shown in FIG. 28 in that the fixed piece 31c is formed to bend by the predetermined angle (angle θ) at vicinities of the grasping pieces 31a, 31b, in a face orthogonal to a horizontal face including the grasping pieces 31a, 31b and in a direction orthogonal to an axial direction of the grasping pieces 31a, 31b.

By constituting such a shapes the way of use of the probe 31 is improved for the measuring person.

Figure 30:
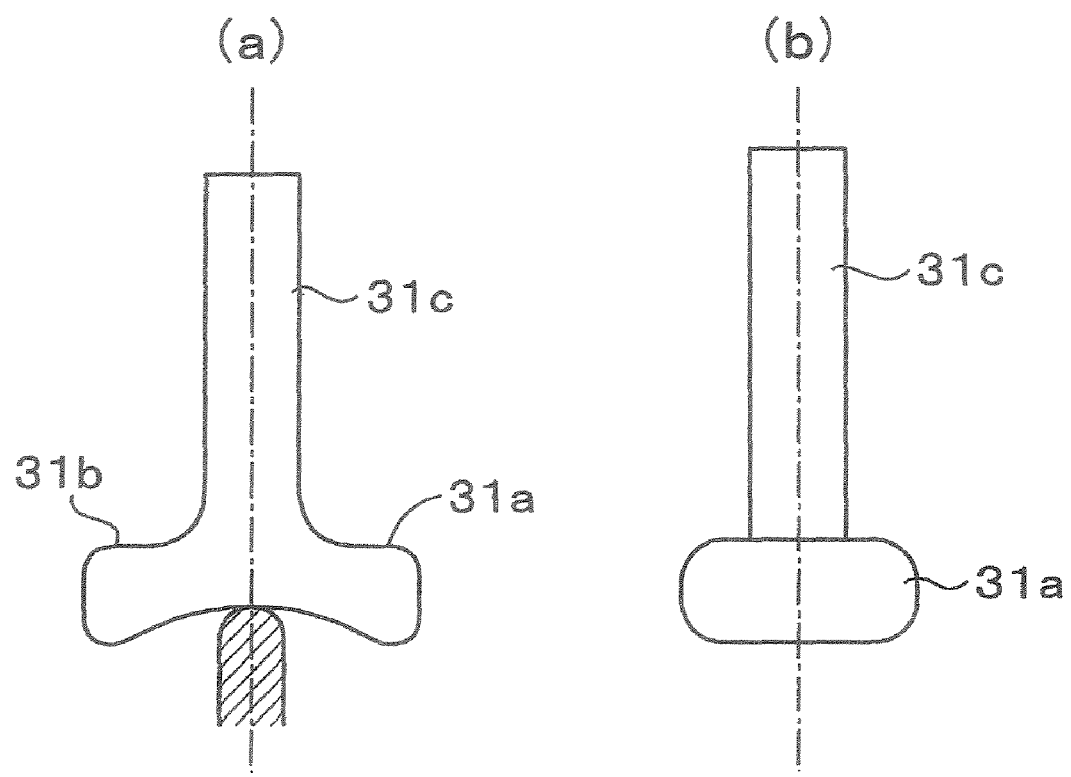
FIG. 30 illustrates views showing an embodiment of a probe in the human spinal column measuring and displaying system according to the invention, FIG. 30($a$) is a front view, FIG. 30($b$) is a side view.

FIG. 30 illustrates views showing an embodiment of a probe in the human spinal column measuring and displaying system according to the invention, FIG. 30(a) is a front view, FIG. 30(b) is a side view.

In FIG. 30(a) and FIG. 30(b), the probe 31 is the same as that of the embodiment shown in FIG. 28 in that the probe 31 is formed substantially in the T-like shape by the grasping pieces 31a, 31b, and the fixed piece 31c.

Further, the grasping pieces 31a, 31b are formed in a recess shape by a predetermined arc (circular arc of radius r) on sides brought into contact with the spinal column. Further, as shown by FIG. 30(b), the grasping piece 31a is formed by an oval shape, although not illustrated.

Further, as shown by FIG. 30(b), the fixed piece 31c differs from that of the embodiment shown in FIG. 28 in that the fixed piece 31c formed by a linear shape.

By constituting such a shape, the way of use of the probe 31 is improved for the measuring person.

Figure 31:
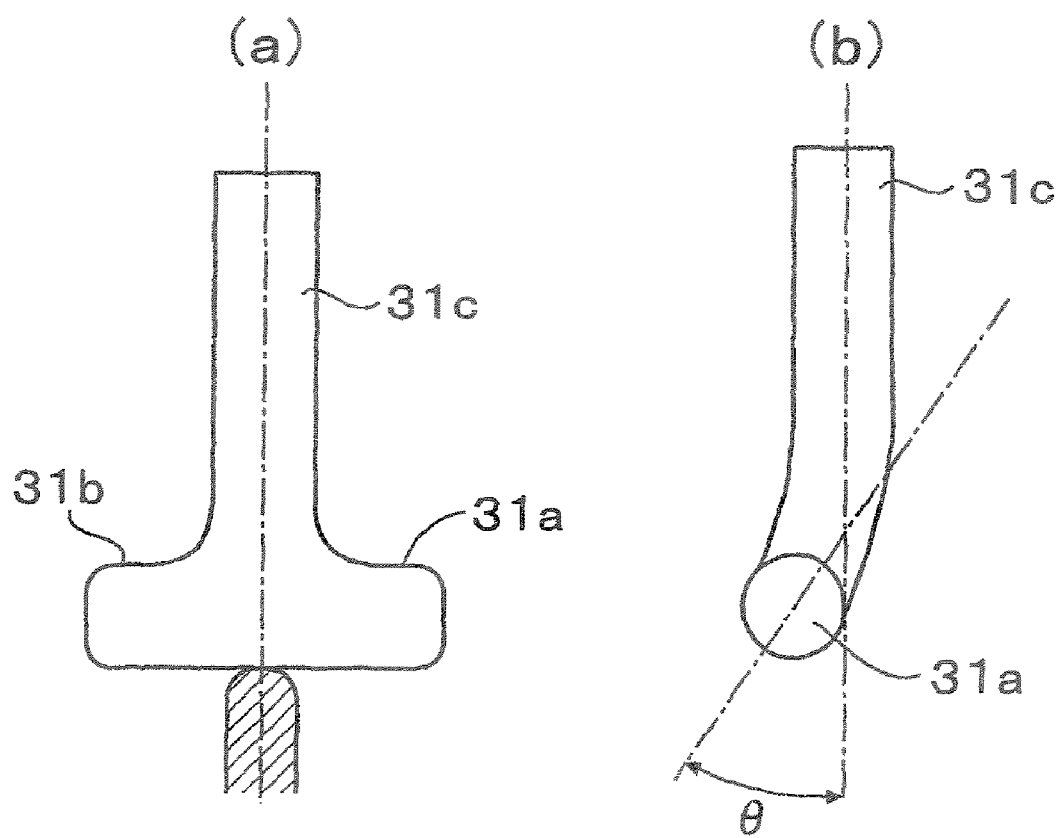
FIG. 31 illustrates views showing an embodiment of a probe in the human spinal column measuring and displaying system according to the invention, FIG. 31($a$) is a front view, FIG. 31($b$) is a side view.

FIG. 31 illustrates views showing an embodiment of a probe in the human spinal column measuring and displaying system according to the invention, FIG. 31(a) is a front view, FIG. 31(b) is a side view.

In FIG. 31(a) and FIG. 31(b), the probe 31 is the same as that of the embodiment shown in FIG. 28 in that the probe 31 is formed substantially by a T-like shape by the grasping pieces 31a, 31b and the fixed piece 31c as shown by FIG. 31(a).

Further, as is also known from FIG. 31(a), the grasping pieces 31(a), 31(b) are formed to be flat on sides brought into contact with the spinal column. Further, the grasping-pieces 31a, 31b are formed by a circular shape in a section thereof as shown by FIG. 31(b).

Further, as shown by FIG. 31(b), the fixed piece 31c is the same as that of the embodiment shown in FIG. 28 in that the fixed piece 31c is formed to bend by the predetermined angle (angle θ) at vicinities of the grasping pieces 31a, 31b, in a face orthogonal to a horizontal face including the grasping pieces 31a, 31b and in a direction orthogonal to an axial direction of the grasping pieces 31a, 31b.

By constituting such a shape, the way of use of the probe 31 is improved for the measuring person.

Figure 32:
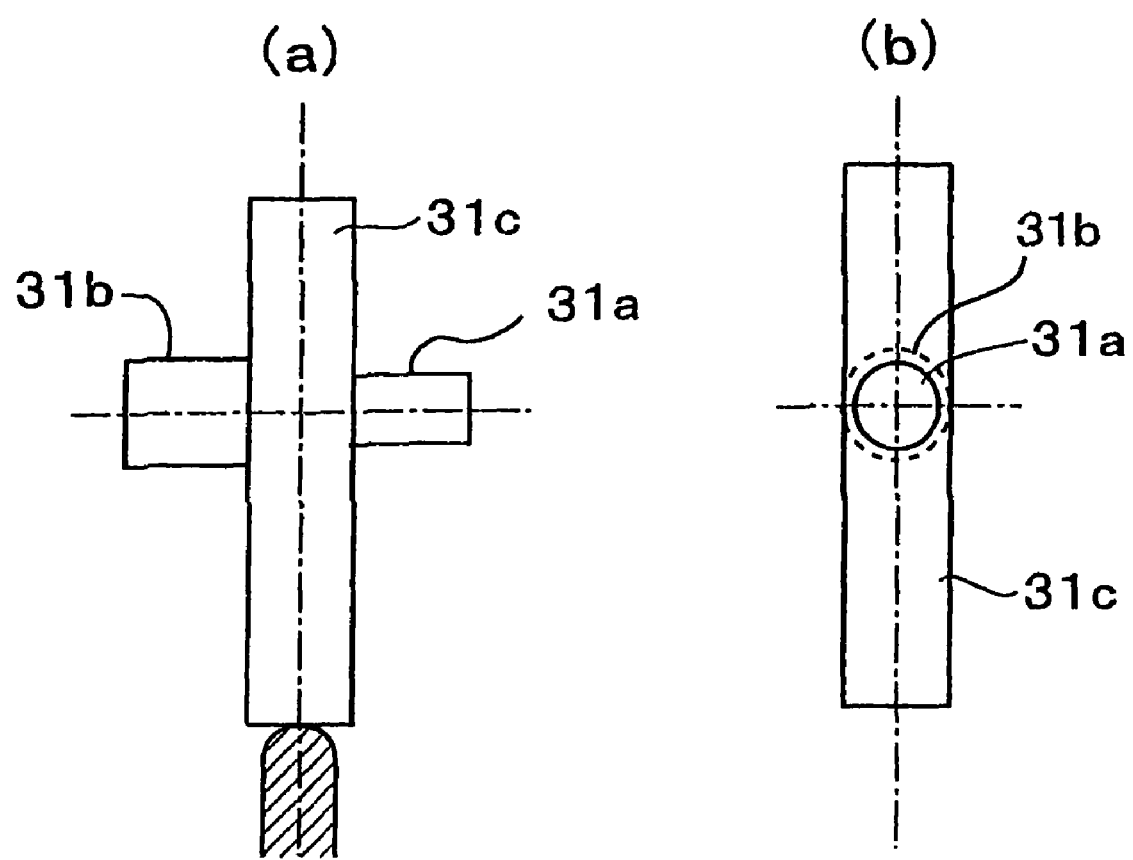
FIG. 32 illustrates views showing an embodiment of a probe in the human spinal column measuring and displaying system according to the invention, FIG. 32($a$) is a front view, FIG. 32($b$) is a side view.

FIG. 32 illustrates views showing an embodiment of a probe in the human spinal column measuring and displaying system according to the invention, FIG. 32(a) is a front view, FIG. 32(b) is a side view.

In FIG. 32, as shown by FIG. 31(a), the probe 31 differs from that of the embodiment shown in FIG. 38 in that the probe 31 is formed substantially by a cross shape by the grasping pieces 31a, 31b which are formed by predetermined lengths and on which the second finger and the third finger of the measuring person touch, and the fixed piece 31c formed by a predetermined length at a center position of the grasping pieces 31a, 31b over both sides of the grasping pieces.

Further, as is also known from FIG. 32(a), a sectional area of one of the grasping pieces 31a, 31b is formed to be larger than a section of other thereof.

By constituting such a shape, the way of use of the probe 31 is improved for the measuring person.

Figure 33:
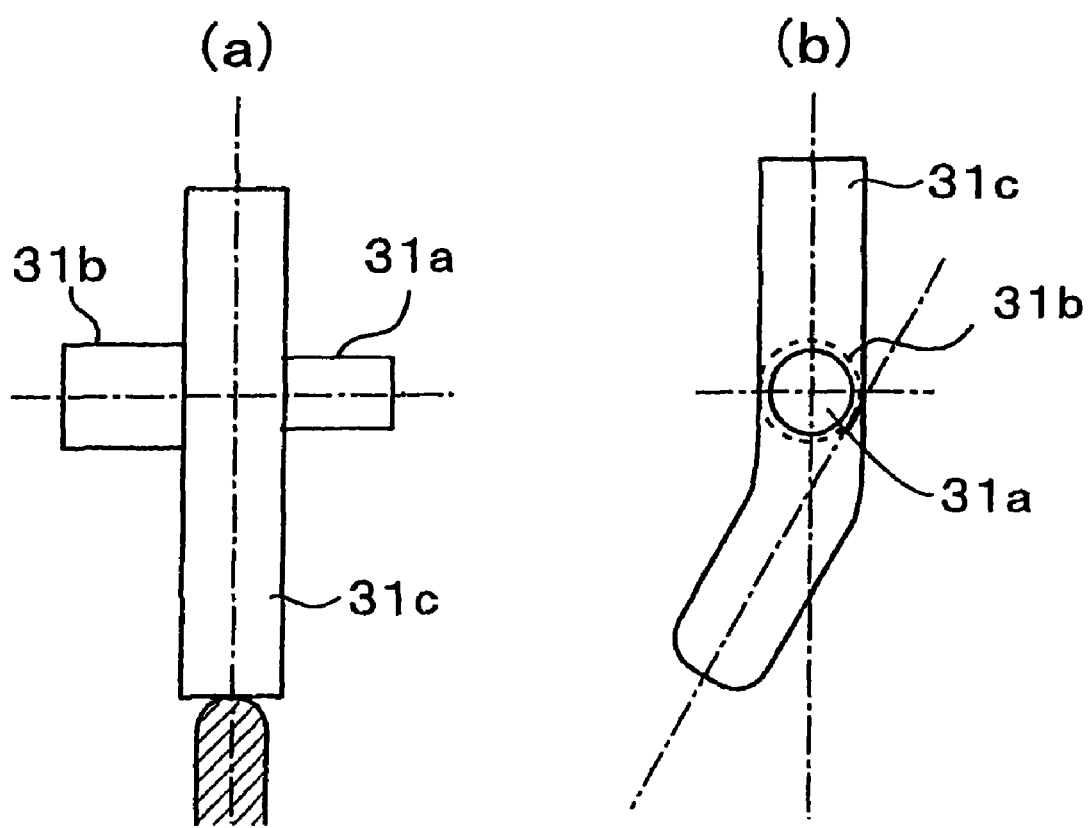
FIG. 33 illustrates views showing an embodiment of a probe in the human spinal column measuring and displaying system according to the invention, FIG. 33($a$) is a front view, FIG. 33($b$) is a side view.

FIG. 33 illustrates views showing an embodiment of a probe in the human spinal column measuring and displaying system according to the invention, FIG. 33(a) is a front view, FIG. 33(b) is a side view.

In FIG. 33(a) and FIG. 33(b), the probe 31 is formed substantially in the cross shape by the grasping pieces 31a, 31b which are formed by predetermined lengths and on which the second finger and the third finger of the measuring person touch, the fixed piece 31c formed by the predetermined length at the center portion of the grasping pieces 31a, 31b, and the distal end of the fixed piece 31c is pivotably fixed to the lower end of the vertical support arm by way of the pivoting shaft.

As shown by FIG. 33(b), the fixed piece 31c is bent by a predetermined angle (θ) on lower sides of the grasping pieces 31a, 31b, in a face orthogonal to a horizontal face including the grasping pieces 31a, 31b and in a direction orthogonal to the axial direction of the grasping pieces 31a, 31b.

As is known also from FIG. 33(a), a sectional area of one of the grasping pieces 31a, 31b is formed to be larger than a sectional area of other thereof.

By constituting such a shape, the way of use of the probe 31 is improved for the measuring person.

The invention claimed is:

1. A human spinal column measuring and displaying system, comprising:
   a spinal column measuring apparatus including
      a measurement bed on which a measurement subject lies in a lying state,
      a base provided on a side of one side face of the measurement bed,
      a measuring direction support arm fixed to the base and configured to be movable in a measuring direction constituting a longitudinal or X axis direction of the measurement bed,
      a parallel support arm fixed to the measuring direction support arm and configured to be movable in a width or Y axis direction orthogonal to the measuring direction,
      a vertical support arm fixed to the parallel support arm and configured to be movable in a thickness or Z axis direction, and
      a probe pivotably fixed to a front end of the vertical support arm to detect amounts of detaching from reference positions in the X direction, the Y direction, the Z direction, and a twist angle θ direction centering on the X axis direction by pinching the probe, which is provided at a front end of a scanning arm configured to move in the X axis direction, the Y axis direction, the Z axis direction, and the twist angle θ direction of the spinal column of the measurement subject on the measurement bed, between a second finger and a third finger of a measuring person and three-dimensionally moving front ends of the second and third fingers in a state of moving the front ends of the second and third fingers from a position of the first cervical vertebra or a position of the first thoracic vertebra to a position of the fifth lumber vertebra of the spinal column of the measurement subject to output as detaching amount measuring data;
   an input apparatus to input a gender and height data of the measurement subject; and
   an image processing apparatus configured to input the detaching amount measuring data from the spinal column measuring apparatus and the gender and height data of the measurement subject from the input apparatus, and to generate a three-dimensional spinal column image of the measurement subject, based on the detaching amount measuring data and the gender and height data of the measurement subject, to provide the spinal column image to a display apparatus,
   wherein the image processing apparatus includes
      converting means for converting the detaching amount measuring data in the X axis direction, the Y axis direction, the Z axis direction, and the θ direction outputted by the spinal column measuring apparatus to predetermined provided data to be stored in a converted data storing unit;

a basic diagram database that stores an average size by the gender and height of the measurement subject and a basic shape of the measurement subject with regard to the respective vertebrae constituting the spinal column of a human body;

data selecting means for selecting to input the respective vertebrae in correspondence with the gender and height data from the basic diagram database in accordance with the gender and height data of the measurement subject inputted by the input apparatus to store in a vertebrae table;

synthesizing means for generating an image of a total of the spinal column constituting a base, based on sizes and shapes of the respective vertebrae stored in the vertebrae table; and an image data generating means for generating the three-dimensional spinal column image of the measurement subject at positions of coordinates in the X direction, the Y direction, the Z direction, and the θ direction of the respective vertebrae based on an image of the total of the spinal column generated by the synthesizing means and the converted data stored in the converted data storing unit, wherein the three-dimensional spinal column image of the measurement subject is generated into a displayable display data by being moved in a predetermined direction or rotated by a predetermined angle so as to be outputted based on a predetermined instruction, wherein the measuring direction support arm includes a moving mechanism including a rail fixed to the base and a slider movably fixed onto the rail;

an attaching seat for attaching the parallel support arm; and one of a pivoting mechanism interposed between the slider of the moving mechanism and the attaching seat to make the attaching seat pivotable in a vertical face;

a pivoting mechanism interposed between the slider of the moving mechanism and the attaching seat to make the attaching seat pivotable in a horizontal face; and a horizontal slide mechanism interposed between the slider of the moving mechanism and the attaching seat to make the attaching seat movable in a horizontal direction.

2. The human spinal column measuring and displaying system according to claim 1, wherein the probe is formed substantially in a T-like shape by grasping pieces that are formed by predetermined lengths and on which the second finger and the third finger of a measuring person touch, and a fixed piece formed by a predetermined length at a center portion of the grasping pieces, a distal end of the fixed piece is pivotably fixed to a lower end of a vertical support arm by a pivoting shaft;

wherein the grasping pieces are formed in a recess shape by a predetermined arc or a planar shape on a side thereof brought into contact with the spinal column.

3. The human spinal column measuring and displaying system according to claim 1, wherein the probe is constituted substantially by a T-like shape by grasping pieces that are formed by predetermined lengths and on which the second finger and the third finger of a measuring person touch, and a fixed piece formed by a predetermined length at a center portion of the grasping pieces, a distal end of the fixed piece is pivotably fixed to a lower end of a vertical support arm;

wherein the fixed piece is bent by a predetermined angle at a vicinity of the grasping piece, in a face orthogonal to a horizontal face including the grasping piece and in a direction orthogonal to an axial direction of the grasping piece.

4. The human spinal column measuring and displaying system according to claim 1, wherein the probe is formed substantially in a cross shape by grasping pieces that are formed by predetermined lengths and on which the second finger and the third finger of a measuring person touch, and a fixed piece formed by a predetermined length over both sides of the grasping pieces at a center portion of the grasping pieces, a distal end of the fixed piece is pivotably fixed to a lower end of a vertical support arm by a pivoting shaft;

wherein the fixed piece is constituted by a linear shape or bent by a predetermined angle at a vicinity of the grasping piece, in a face orthogonal to the horizontal face including the grasping piece and in a direction orthogonal to an axial direction of the grasping piece.

5. The human spinal column measuring and displaying system according to claim 1, wherein a sectional area of one of the grasping pieces is formed to be larger than a sectional area of other thereof.

6. The human spinal column measuring and displaying system according to claim 2, wherein a sectional area of one of the grasping pieces is formed to be larger than a sectional area of other thereof.

7. The human spinal column measuring and displaying system according to claim 3, wherein a sectional area of one of the grasping pieces is formed to be larger than a sectional area of other thereof.

8. The human spinal column measuring and displaying system according to claim 4, wherein a sectional area of one of the grasping pieces is formed to be larger than a sectional area of other thereof.

9. A human spinal column measuring and displaying system, comprising:

a spinal column measuring apparatus including a measurement bed on which a measurement subject lies in a lying state, a base provided on a side of one side face of the measurement bed, a measuring direction support arm fixed to the base and configured to be movable in a measuring direction constituting a longitudinal or X axis direction of the measurement bed, a parallel support arm fixed to the measuring direction support arm and configured to be movable in a width or Y axis direction orthogonal to the measuring direction, a vertical support arm fixed to the parallel support arm and configured to be movable in a thickness or Z axis direction, and a probe pivotably fixed to a front end of the vertical support arm to detect amounts of detaching from reference positions in the X axis direction, the Y axis direction, the Z axis direction, and a twist angle θ direction centering on the X axis direction by pinching the probe, which is provided at a front end of a scanning arm configured to move in the X axis direction, the Y axis direction, the Z axis direction, and the twist angle θ direction of the spinal column of the measurement subject on the measurement bed, between a second finger and a third finger of a measuring person and three-dimensionally moving front ends of the first and second fingers in a state of moving the front ends of the first and second fingers from a position of the first cervical vertebra or a position of the first thoracic vertebra to a position of the fifth lumber vertebra of the spinal column of the measurement subject to output as detaching amount measuring data;

an input apparatus to input a gender and height data of the measurement subject; and an image processing apparatus configured to input the detaching amount measuring data from the spinal column measuring apparatus and the gender and height data of the measurement subject from the input apparatus, and to generate a three-dimensional spinal column image of the measurement subject, based on the detaching amount measuring data and the gender and height data of the measurement subject, to provide the spinal column image to a display apparatus;

wherein the image processing apparatus includes converting means for converting the detaching amount measuring data in the X axis direction, the Y axis direction, the Z axis direction, and the θ direction outputted by the spinal column measuring apparatus to predetermined provided data to be stored in a converted data storing unit;

a basic diagram database that stores an average size by the gender and height of the measurement subject and a basic shape of the measurement subject with regard to the respective vertebrae constituting the spinal column of a human body;

data selecting means for selecting to input the respective vertebrae in correspondence with the gender and height data from the basic diagram database in accordance with the gender and height data of the measurement subject inputted by the input apparatus to store in a vertebrae table;

synthesizing means for generating an image of a total of the spinal column constituting a base, based on sizes and shapes of the respective vertebrae stored in the vertebrae table; and an image data generating means for generating the three-dimensional spinal column image of the measurement subject at positions of coordinates in the X direction, the Y direction, the Z direction, and the θ direction of the respective vertebra; based on an image of the total of the spinal column generated by the synthesizing means and the converted data stored in the converted data storing unit, wherein the three-dimensional spinal column image of the measurement subject is generated into a displayable display data by being moved in a predetermined direction or rotated by a predetermined angle so as to be outputted based on a predetermined instruction; and the measurement bed is constituted by a base portion installed on a floor, a fixed base fixed onto the base portion, and a movable mechanism including a moving base horizontally movable on the fixed base, and a bed sheet portion fixed onto the moving base of the movable mechanism.

10. The human spinal column measuring and displaying system according to claim 9, wherein the probe is formed substantially in a T-like shape by grasping pieces that are formed by predetermined lengths and on which the second finger and the third finger of a measuring person touch, and a fixed piece formed by a predetermined length at a center portion of the grasping pieces, a distal end of the fixed piece is pivotably fixed to a lower end of a vertical support arm by a pivoting shaft;

wherein the grasping pieces are formed in a recess shape by a predetermined arc or a planar shape on a side thereof brought into contact with the spinal column.

11. The human spinal column measuring and displaying system according to claim 9, wherein the probe is constituted substantially by a T-like shape by grasping pieces that are formed by predetermined lengths and on which the second finger and the third finger of a measuring person touch, and a fixed piece formed by a predetermined length at a center portion of the grasping pieces, a distal end of the fixed piece is pivotably fixed to a lower end of a vertical support arm;

wherein the fixed piece is bent by a predetermined angle at a vicinity of the grasping piece, in a face orthogonal to a horizontal face including the grasping piece and in a direction orthogonal to an axial direction of the grasping piece.

12. The human spinal column measuring and displaying system according to claim 9, wherein the probe is formed substantially in a cross shape by grasping pieces that are formed by predetermined lengths and on which the second finger and the third finger of a measuring person touch, and a fixed piece formed by a predetermined length over both sides of the grasping pieces at a center portion of the grasping pieces, a distal end of the fixed piece is pivotably fixed to a lower end of a vertical support arm by a pivoting shaft;

wherein the fixed piece is constituted by a linear shape or bent by a predetermined angle at a vicinity of the grasping piece, in a face orthogonal to the horizontal face including the grasping piece and in a direction orthogonal to an axial direction of the grasping piece.

13. The human spinal column measuring and displaying system according to claim 9, wherein a sectional area of one of the grasping pieces is formed to be larger than a sectional area of other thereof.

14. The human spinal column measuring and displaying system according to claim 10, wherein a sectional area of one of the grasping pieces is formed to be larger than a sectional area of other thereof.

15. The human spinal column measuring and displaying system according to claim 11, wherein a sectional area of one of the grasping pieces is formed to be larger than a sectional area of other thereof.

16. The human spinal column measuring and displaying system according to claim 12, wherein a sectional area of one of the grasping pieces is formed to be larger than a sectional area of other thereof.

* * * * *